US007294490B2

(12) United States Patent
Romond et al.

(10) Patent No.: US 7,294,490 B2
(45) Date of Patent: Nov. 13, 2007

(54) METHOD FOR DETECTING MICROORGANISMS

(75) Inventors: Pierre-Charles Romond, Orcet (FR); Michel Renaud, deceased, late of Le Cendre (FR); by Johanne Renaud, legal representative, Clermont-Ferrand (FR); by Mathias Renaud, legal representative, Plougastel (FR); Monique Alric, Clermont-Ferrand (FR); Olivier Meiniel, Cournon d'Auvergne (FR); Lionel Ballut, Chamaliere (FR)

(73) Assignee: Compagnie Gervais Danone, Levallois-Perret (FR)

( * ) Notice: Subject to any disclaimer, the term of this patent is extended or adjusted under 35 U.S.C. 154(b) by 413 days.

(21) Appl. No.: 10/722,555

(22) Filed: Nov. 28, 2003

(65) Prior Publication Data
US 2005/0130169 A1   Jun. 16, 2005

Related U.S. Application Data

(63) Continuation of application No. 10/333,338, filed as application No. PCT/FR01/02371 on Jul. 20, 2001, now abandoned.

(30) Foreign Application Priority Data
Jul. 21, 2000 (FR) .................................. 00 09600
Oct. 2, 2000 (FR) .................................. 00 12524

(51) Int. Cl.
C12P 19/34 (2006.01)
(52) U.S. Cl. .................................... 435/91.2
(58) Field of Classification Search ............... 435/91.1, 435/91.2, 6
See application file for complete search history.

(56) References Cited

U.S. PATENT DOCUMENTS

| 5,536,638 | A |   | 7/1996  | Rossau et al. |
| 5,708,160 | A |   | 1/1998  | Goh et al. |
| 5,756,293 | A |   | 5/1998  | Hall et al. |
| 5,786,147 | A |   | 7/1998  | Mabilat et al. |
| 5,989,821 | A | * | 11/1999 | Goh et al. ................ 435/6 |

FOREIGN PATENT DOCUMENTS

| EP | 0 943 010 | 3/2002 |
| FR | 2 752 425 | 2/1998 |

OTHER PUBLICATIONS

Todar's Online Textbook of Bacteriology, http://www.textbookofbacteriology.net/normalflora.html, pp. 1-20, Kenneth Todar University of Wisconsin-Madison Department of Bacteriology, 2002.*
Planet et al. Current Microbiology, vol. 30, pp. 137-141, 1995.*
Bergsland et al. Journal of Bacteriology, vol. 173, No. 11, pp. 3446-3455, 1991.*
Dennis, P. The Journal of Biological Chemistry, vol. 259, No. 5, pp. 3202-3209, 1984.*
Hosami Harada et al; Phylogenetical relationship based on groE genes among phenotypically related *Enterobacter, Pantoea, Klebesiella, Serratia* and *Erwinia* species: Journal of General and Applied Microbiology, vol. 43, No. 6, pp. 355-361, 1997.
Natalya Zakharova et al; Fused and overlapping rpoB and rpoC geners in *Helicobacters, Campylobacters*, and related bacteria: Journal of Bacteriology, vol. 181, No. 12, pp. 3857-3859, 1999.
Patricia Renesto et al; "rpoB gene analysis as a novel strategy for identification of spirochetes from the genera *Borrelia, Treponema*, and *Leptospira*": Journal of Clinical Microbiology, vol. 38, No. 6, pp. 2200-22203, 2000.
B.C. Love et al' "Cloning and sequence of the groESL heat-shock operon of *Pasteurella multocida*": Gene, vol. 166, No. 1, pp. 179-180, 1998.
T. Ohta et al.; "Molecular characterization of the gene operon of heat chock proteins HSP60 and HSP10 in methicullin-resistant *Staphyloccoddus aureus*": Biochemical and Biophysical Research Communications, vol. 193, No. 2, pp. 730-737, Jun. 15, 1993.
A. Franks et al; "Variations of Bacterial Populations in Human Feces Measured by Fluorescent in Situ Hybridization with Group-Specific 16S rRNA-Targeted Oligonucleotide Probes"; Applied and Environmental Microbiology, vol. 64, No. 9, pp. 3336-3345; Sep. 1998.
Abdelghani Sghir et al: "Quantification of bacterial groups within human fecal flora by oliognucleotide probe hybridization": Applied and Environmental Microbiology, vol. 66, No. 5, pp. 2263-2266, 2000.
C. Mollet et al; "RPOB Sequence Analysis as a Novel Basis for Bacterial Identification": Molecular Microbiology, vol. 26, No. 5, pp. 1005-1011, 1997.
Greisen et al. "Staphylococcal identification using PCR amplification of 16SrRna genes" Journal of Clinical Microbiology, vol. 32, pp. 335-351, 1994.
Jensen et al; "Staphylococcal identification using PCR amplification of spacer regions between 16S and 23S genetic loci"; Applied Environmental Microbiology, vol. 59, pp. 945-952, 1994.

(Continued)

*Primary Examiner*—Gary Benzion
*Assistant Examiner*—Cynthia B Wilder
(74) *Attorney, Agent, or Firm*—Oblon, Spivak, McClelland, Maier & Neustadt, P.C.

(57) ABSTRACT

The invention concerns a method for detecting microorganisms constituting a flora of micro-organisms, whereof at least part of the elements has a common operon. The invention is characterised in that it consists in identifying the elements of said flora by studying the intergenetic sequence of said operon, and the support exhibiting nucleic acids capable of hybridizing said intergenetic sequence.

5 Claims, 6 Drawing Sheets

OTHER PUBLICATIONS

Pilkaytis et al; "Differentiation of Slowly Growing Mycobacterium Species, Including *Mycobacterium tuberculosis*, by Gene Amplification and Restriction Fragment Length Polymorphism Analysis"; Journal of Clinical Microbiology, vol. 30, No. 7, Jul. 1992, pp. 1815-1822.

Zoetendal et al; "Temperature gradient gel electrophoresis analysis of 16 S rRNA from human fecal samples reveals stable and host-specific communities of active bacteria"; vol. 64, No. 10, pp. 3854-3859; Oct. 1998.

Vaitilinggom et al.; "Direct detection of viable bacterial, molds, and yeast by reverse transcriptase PCR in contaminated milk samples after heat treatment"; Applied Environmental Microbiology; vol. 64, pp. 1157-1160; 1998.

Emelyanov et al; "A GroE-based phylogenetic analysis shows a very close evolutionary relationship between mitochondria and rickettsia"; Russian Journal of Genetics, vol. 35, pp. 618-627, 1999.

A. Telentia, et al.; "Rapid Identification of Mycobacterial to the Species Level by Polymerase Chain Reaction and Restriction Enzyme Analysis"; Journal of Clinical Microbiology, vol. 31, No. 2, Feb. 1993, pp. 175-178.

A. Suau, et al. "Direct Analysis of Genes Encoding 16S rRna from Complex Communities Reveals Many Novel Molecular Species within the Human Gut"; Applied and Environmental Microbiology, vol. 65, No. 11, pp. 4799-4807; Nov. 1999.

* cited by examiner

SEQUENCE LISTING

```
<160> NUMBER OF SEQ ID NOS: 189

<210> SEQ ID NO 1
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t

<400> SEQUENCE: 1
ggngayaary tngcnggnag ncaygg                                           26

<210> SEQ ID NO 2
<211> LENGTH: 26
<212> TYPE: DNA
<213> ORGANISM: Artificial sequence
```

```
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t

<400> SEQUENCE: 2
ggngayaary tngcnggncg ncaygg                                  26

<210> SEQ ID NO 3
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (21)
<223> OTHER INFORMATION: n = a, g, c or t

<400> SEQUENCE: 3
ggngayaary tngcnaayag ncaygg                                  26

<210> SEQ ID NO 4
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
```

<223> OTHER INFORMATION: n = a, g, c or t
<220> FEATURE:
<221> NAME/KEY: misc_feature
<222> LOCATION: (21)
<223> OTHER INFORMATION: n = a, g, c or t

<400> SEQUENCE: 4
ggngayaary tngcnaaycg ncaygg                               26

<210> SEQ ID NO 5
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t

<400> SEQUENCE: 5
ggngayaara tggcnggnmg ncaygg                               26

<210> SEQ ID NO 6
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t

<400> SEQUENCE: 6
ggngayaart tygcntcnmg ncaygg                               26

<210> SEQ ID NO 7
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms

```
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (21)
<223> OTHER INFORMATION: n = a, g, c or t

<400> SEQUENCE: 7
ggngayaart tygcnagymg ncaygg                                            26

<210> SEQ ID NO 8
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t

<400> SEQUENCE: 8
ggngayaart tygcnacnmg ncaygg                                            26

<210> SEQ ID NO 9
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (18)
<223> OTHER INFORMATION: n = a, g, c or t

<400> SEQUENCE: 9
aaygcngayt tygayggnga ycarat                                            26

<210> SEQ ID NO 10
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
```

```
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (18)
<223> OTHER INFORMATION: n = a, g, c or t

<400> SEQUENCE: 10
aaygcngayt tgayggnca ratggc                                              26

<210> SEQ ID NO 11
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (18)
<223> OTHER INFORMATION: n = a, g, c or t

<400> SEQUENCE: 11
aaygcngayt tgayggnga ygarat                                              26

<210> SEQ ID NO 12
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (18)
<223> OTHER INFORMATION: n = a, g, c or t

<400> SEQUENCE: 12
ggnggncarm gnttyggnga ratgga                                             26

<210> SEQ ID NO 13
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
```

```
<222> LOCATION: (6)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (18)
<223> OTHER INFORMATION: n = a, g, c or t

<400> SEQUENCE: 13
ggnggncayg gnttygnga ratgga                                26

<210> SEQ ID NO 14
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (18)
<223> OTHER INFORMATION: n = a, g, c or t

<400> SEQUENCE: 14
ggnggncarw snttygnga ratgga                                26

<210> SEQ ID NO 15
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (6)..(7)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (18)
<223> OTHER INFORMATION: n = a, g, c or t

<400> SEQUENCE: 15
ggnggnntnm gnttygnga ratgga                                26
```

<210> SEQ ID NO 16
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 16
ggnaarcgng tngaytaytc nggnmg                                        26

<210> SEQ ID NO 17
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 17
ggnaarcgng tngaytayag nggnmg                                        26

<210> SEQ ID NO 18
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature

```
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 18
ggnaaragng tngaytaytc nggnmg                                    26

<210> SEQ ID NO 19
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 19
ggnaaragng tngaytayag nggnmg                                    26

<210> SEQ ID NO 20
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
```

```
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 20
ggnaarcgng gngaytaytc ngtnmg                                          26

<210> SEQ ID NO 21
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 21
ggnaarcgng gngaytayag ngtnmg                                          26

<210> SEQ ID NO 22
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 22
ggnaaragng gngaytaytc ngtnmg                                          26
```

<210> SEQ ID NO 23
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 23
ggnaaragng gngaytayag ngtnmg                                    26

<210> SEQ ID NO 24
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 24
ggnaarcgng tngayttytc nggnmg                                    26

<210> SEQ ID NO 25
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:

<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 25
ggnaarcgng tngayttyag nggnmg                                   26

<210> SEQ ID NO 26
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 26
ggnaaragng tngayttytc nggnmg                                   26

<210> SEQ ID NO 27
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t

```
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 27
ggnaaragng tngayttyag nggnmg                                             26

<210> SEQ ID NO 28
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 28
ggnaarcgng tngayttytc ngcnmg                                             26

<210> SEQ ID NO 29
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 29
```
ggnaarcgng tngayttyag ngcnmg                                  26

<210> SEQ ID NO 30
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 30
ggnaaragng tngayttytc ngcnmg                                  26

<210> SEQ ID NO 31
<211> LENGTH: 26
<212> TYPE: DNA
<213> ORGANISM: Artificial sequence
<220> FEATURE:
<223> OTHER INFORMATION: Description of artificial sequence: Primer
      for detecting the amplification of the intergenic
      region of the rpoBC operon of micro-organisms
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 31
ggnaaragng tngayttyag ngcnmg                                  26

<210> SEQ ID NO 32
<211> LENGTH: 26
<212> TYPE: DNA
<213> ORGANISM: Artificial sequence
<220> FEATURE:
<223> OTHER INFORMATION: Description of artificial sequence: Primer
      corresponding to a proteinic motive of HSP10
      from Escherichia Coli.

```
<220> FEATURE:
<221> NAME/KEY: misc_feature
<222> LOCATION: (15)
<223> OTHER INFORMATION: n = a, g, c or t

<400> SEQUENCE: 32
ctggaygtka arrtnggyga yatygt                                        26

<210> SEQ ID NO 33
<211> LENGTH: 26
<212> TYPE: DNA
<213> ORGANISM: Artificial sequence
<220> FEATURE:
<223> OTHER INFORMATION: Description of artificial sequence: Primer
      corresponding to a proteinic motive of HSP10
      from Escherichia Coli.
<220> FEATURE:
<221> NAME/KEY: misc_feature
<222> LOCATION: (2)..(3)
<223> OTHER INFORMATION: n = a, g, c or t
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (9)
<223> OTHER INFORMATION: n = a, g, c or t

<400> SEQUENCE: 33
annacngtng crgtrgtggt rccgtc                                        26

<210> SEQ ID NO 34
<211> LENGTH: 26
<212> TYPE: DNA
<213> ORGANISM: Artificial sequence
<220> FEATURE:
<223> OTHER INFORMATION: Description of artificial sequence: Consensus
      Primer (UNI-ADEG 1)
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)..(25)
<223> OTHER INFORMATION: n = a, g, c or t

<400> SEQUENCE: 34
ggngayggna cnacnacngc nacnnt                                        26

<210> SEQ ID NO 35
<211> LENGTH: 26
```

```
<212> TYPE: DNA
<213> ORGANISM: Artificial sequence
<220> FEATURE:
<223> OTHER INFORMATION: Description of artificial sequence: Consensus
      Primer (UNI-ADEG 2)
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)..(25)
<223> OTHER INFORMATION: n = a, g, c or t

<400> SEQUENCE: 35
ggngayggna cnacnacntg ntcnnt                                            26

<210> SEQ ID NO 36
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting enterobacteria (ENT-BNEW).
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 36
aanmttcgtc cnytrcanga ycgngt                                            26

<210> SEQ ID NO 37
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting clostridia (CLO-BNEW2)
<220> FEATURE:
<221> NAME/KEY: misc_feature
<222> LOCATION: (3)
<223> OTHER INFORMATION: n = a, g, c or t
```

-continued

```
<220> FEATURE:
<221> NAME/KEY: misc_feature
<222> LOCATION: (21)
<223> OTHER INFORMATION: n = a, g, c or t

<400> SEQUENCE: 37
atnarrccay twggwgaymg ngtwgt                                          26

<210> SEQ ID NO 38
<211> LENGTH: 26
<212> TYPE: DNA
<213> ORGANISM: Artificial sequence
<220> FEATURE:
<223> OTHER INFORMATION: Description of artificial sequence:  Consensus
      sequence for detecting bifidobacteria (BIF-BNEW).
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t

<400> SEQUENCE: 38
aarccrctcg aggacmrnrt nstsgt                                          26

<210> SEQ ID NO 39
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Lactococcus (UNI-A3).
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)..(25)
<223> OTHER INFORMATION: n = a, g, c or t

<400> SEQUENCE: 39
ggngayggna cnaanacngc nacnnt                                          26

<210> SEQ ID NO 40
<211> LENGTH: 26
<212> TYPE: DNA
<213> ORGANISM: Artificial sequence
<220> FEATURE:
<223> OTHER INFORMATION: Description of artificial sequence:  Consensus
      sequence for detecting Bifidobacterium and Mycobacterium
```

```
      (BIF-BNEW2).
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 40
atcaagccnc tmgrrgacmr srtnst                                          26

<210> SEQ ID NO 41
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Helicobacter (HEL-BNEW).
<220> FEATURE:
<221> NAME/KEY: misc_feature
<222> LOCATION: (1)
<223> OTHER INFORMATION: n = a, g, c or t
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 41
ntncanccnt tnggnganag ngtntt                                          26

<210> SEQ ID NO 42
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Campylobacter (CAM-BNEW).
<220> FEATURE:
<221> NAME/KEY: misc_feature
<222> LOCATION: (1)
<223> OTHER INFORMATION: n = a, g, c or t
<220> FEATURE:
<221> NAME/KEY: misc_feature
<222> LOCATION: (3)
<223> OTHER INFORMATION: n = a, g, c or t
```

```
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 42
ntncanccnt tnggnaancg ngtnct                                          26

<210> SEQ ID NO 43
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting bacteroids (BACT-BNEW).
<220> FEATURE:
<221> NAME/KEY: misc_feature
<222> LOCATION: (1)
<223> OTHER INFORMATION: n = a, g, c or t
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 43
```

```
ntnaanccnt tngcngancg ngtnct                                              26

<210> SEQ ID NO 44
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Chlamydia (CHLA-BNEW).
<220> FEATURE:
<221> NAME/KEY: misc_feature
<222> LOCATION: (1)
<223> OTHER INFORMATION: n = a, g, c or t
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 44
ntnaanccnt tnggnganag natntt                                              26

<210> SEQ ID NO 45
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Mycoplasma (MYCP-BNEW).
<220> FEATURE:
<221> NAME/KEY: misc_feature
<222> LOCATION: (1)
<223> OTHER INFORMATION: n = a, g, c or t
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)..(10)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
```

```
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 45
ntnaaaccnn tnggnaancg ngtnat                                       26

<210> SEQ ID NO 46
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Staphylococcus (STA-BNEW).
<220> FEATURE:
<221> NAME/KEY: misc_feature
<222> LOCATION: (1)
<223> OTHER INFORMATION: n = a, g, c or t
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (9)..(10)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 46
ntnaaaccnn tnggnaancg ngtnat                                       26

<210> SEQ ID NO 47
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Lactoccocus and Streptococcus (LACC-BNEW).
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (14)
<223> OTHER INFORMATION: n = a, g, c or t
```

<400> SEQUENCE: 47
ttgaaaccnt tagngraycg ygtrst                    26

<210> SEQ ID NO 48
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Lactobacillus and Bacillus (LACB-BNEW).
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 48
ttamarccaw tmggngatcg ngtnrt                    26

<210> SEQ ID NO 49
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Clostridium (CLO-BNEW3).
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (5)
<223> OTHER INFORMATION: n = a, g, c or t
<220> FEATURE:
<221> NAME/KEY: misc_feature
<222> LOCATION: (10)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 49
atnanaccan tnggngacag ngtngt                    26

<210> SEQ ID NO 50
<211> LENGTH: 26
<212> TYPE: DNA
<213> ORGANISM: Artificial sequence
<220> FEATURE:
<223> OTHER INFORMATION: Description of artificial sequence:  Consensus
      sequence for detecting Enterobacteriaceae, Pasteurella,

```
        Haemophilus (ENT-BNEW2).
<220> FEATURE:
<221> NAME/KEY: misc_feature
<222> LOCATION: (1)
<223> OTHER INFORMATION: n = a, g, c or t
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 50
ntncgnccnt tncangancg ngtnat                                          26

<210> SEQ ID NO 51
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Neisseria, Legionella (LEG-BNEW).
<220> FEATURE:
<221> NAME/KEY: misc_feature
<222> LOCATION: (1)
<223> OTHER INFORMATION: n = a, g, c or t
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
```

```
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 51
ntncgnccnt tncangancg ngtngt                                              26

<210> SEQ ID NO 52
<211> LENGTH: 26
<212> TYPE: DNA
<213> ORGANISM: Artificial sequence
<220> FEATURE:
<223> OTHER INFORMATION: Description of artificial sequence: Consensus
      sequence for detecting Aeromonas and Bordetella (AER-BNEW).
<220> FEATURE:
<221> NAME/KEY: misc_feature
<222> LOCATION: (1)
<223> OTHER INFORMATION: n = a, g, c or t
<220> FEATURE:
<221> NAME/KEY: misc_feature
<222> LOCATION: (3)
<223> OTHER INFORMATION: n = a, g, c or t
<220> FEATURE:
<221> NAME/KEY: misc_feature
<222> LOCATION: (6)
<223> OTHER INFORMATION: n = a, g, c or t
<220> FEATURE:
<221> NAME/KEY: misc_feature
<222> LOCATION: (9)
<223> OTHER INFORMATION: n = a, g, c or t
<220> FEATURE:
<221> NAME/KEY: misc_feature
<222> LOCATION: (12)
<223> OTHER INFORMATION: n = a, g, c or t
<220> FEATURE:
<221> NAME/KEY: misc_feature
<222> LOCATION: (15)
<223> OTHER INFORMATION: n = a, g, c or t
<220> FEATURE:
<221> NAME/KEY: misc_feature
<222> LOCATION: (18)
<223> OTHER INFORMATION: n = a, g, c or t
<220> FEATURE:
<221> NAME/KEY: misc_feature
<222> LOCATION: (21)
<223> OTHER INFORMATION: n = a, g, c or t
<220> FEATURE:
<221> NAME/KEY: misc_feature
<222> LOCATION: (24)
<223> OTHER INFORMATION: n = a, g, c or t

<400> SEQUENCE: 52
ntncgnccnc tncangancg ngtnat                                              26

<210> SEQ ID NO 53
<211> LENGTH: 26
<212> TYPE: DNA
<213> ORGANISM: Artificial sequence
<220> FEATURE:
<223> OTHER INFORMATION: Description of artificial sequence: Primer
<220> FEATURE:
<221> NAME/KEY: misc_feature
<222> LOCATION: (3)
<223> OTHER INFORMATION: n = a, g, c or t/u
<220> FEATURE:
<221> NAME/KEY: misc_feature
<222> LOCATION: (6)
<223> OTHER INFORMATION: n = a, g, c or t/u
<220> FEATURE:
<221> NAME/KEY: misc_feature
<222> LOCATION: (9)..(10)
```

```
<223> OTHER INFORMATION: n = a, g, c or t/u
<220> FEATURE:
<221> NAME/KEY: misc_feature
<222> LOCATION: (12)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u

<400> SEQUENCE: 53
ggnggncann snttyggnga ratgga                                    26

<210> SEQ ID NO 54
<211> LENGTH: 26
<212> TYPE: DNA
<213> ORGANISM: Artificial sequence
<220> FEATURE:
<223> OTHER INFORMATION: Description of artificial sequence: Primer
<220> FEATURE:
<221> NAME/KEY: misc_feature
<222> LOCATION: (6)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u

<400> SEQUENCE: 54
aaygcngayt tygayggnga ysarat                                    26

<210> SEQ ID NO 55
<211> LENGTH: 26
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (3)
<223> OTHER INFORMATION: n = a, g, c or t/u
<220> FEATURE:
<221> NAME/KEY: misc_feature
<222> LOCATION: (6)
<223> OTHER INFORMATION: n = a, g, c or t/u
<220> FEATURE:
<221> NAME/KEY: misc_feature
<222> LOCATION: (12)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u

<400> SEQUENCE: 55
ggnggncarm gnttyggnga ratgga                                    26

<210> SEQ ID NO 56
<211> LENGTH: 26
<212> TYPE: DNA
<213> ORGANISM: Artificial sequence
<220> FEATURE:
<223> OTHER INFORMATION: Description of artificial sequence: Primer
<220> FEATURE:
<221> NAME/KEY: misc_feature
<222> LOCATION: (3)
<223> OTHER INFORMATION: n = a, g, c or t/u
<220> FEATURE:
<221> NAME/KEY: misc_feature
<222> LOCATION: (6)
<223> OTHER INFORMATION: n = a, g, c or t/u
<220> FEATURE:
<221> NAME/KEY: misc_feature
```

```
<222> LOCATION: (12)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u

<400> SEQUENCE: 56
ggnggncayg gnttyggnga ratgga                                              26

<210> SEQ ID NO 57
<211> LENGTH: 26
<212> TYPE: DNA
<213> ORGANISM: Artificial sequence
<220> FEATURE:
<223> OTHER INFORMATION: Description of artificial sequence: Primer
<220> FEATURE:
<221> NAME/KEY: misc_feature
<222> LOCATION: (3)
<223> OTHER INFORMATION: n = a, g, c or t/u
<220> FEATURE:
<221> NAME/KEY: misc_feature
<222> LOCATION: (6)
<223> OTHER INFORMATION: n = a, g, c or t/u
<220> FEATURE:
<221> NAME/KEY: misc_feature
<222> LOCATION: (12)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u

<400> SEQUENCE: 57
ggnggncarw snttyggnga ratgga                                              26

<210> SEQ ID NO 58
<211> LENGTH: 26
<212> TYPE: DNA
<213> ORGANISM: Artificial sequence
<220> FEATURE:
<223> OTHER INFORMATION: Description of artificial sequence: Primer
<220> FEATURE:
<221> NAME/KEY: misc_feature
<222> LOCATION: (3)
<223> OTHER INFORMATION: n = a, g, c or t/u
<220> FEATURE:
<221> NAME/KEY: misc_feature
<222> LOCATION: (6)..(7)
<223> OTHER INFORMATION: n = a, g, c or t/u
<220> FEATURE:
<221> NAME/KEY: misc_feature
<222> LOCATION: (9)
<223> OTHER INFORMATION: n = a, g, c or t/u
<220> FEATURE:
<221> NAME/KEY: misc_feature
<222> LOCATION: (12)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u

<400> SEQUENCE: 58
ggnggnntnm gnttyggnga ratgga                                              26

<210> SEQ ID NO 59
<211> LENGTH: 26
<212> TYPE: DNA
<213> ORGANISM: Artificial sequence
<220> FEATURE:
<223> OTHER INFORMATION: Description of artificial sequence: Primer
<220> FEATURE:
```

```
<221> NAME/KEY: misc_feature
<222> LOCATION: (6)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u

<400> SEQUENCE: 59
aaygcngayt tgayggnga ycarat                                          26

<210> SEQ ID NO 60
<211> LENGTH: 26
<212> TYPE: DNA
<213> ORGANISM: Artificial sequence
<220> FEATURE:
<223> OTHER INFORMATION: Description of artificial sequence: Primer
<220> FEATURE:
<221> NAME/KEY: misc_feature
<222> LOCATION: (6)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u

<400> SEQUENCE: 60
aaygcngayt tgayggnca ratggc                                          26

<210> SEQ ID NO 61
<211> LENGTH: 26
<212> TYPE: DNA
<213> ORGANISM: Artificial sequence
<220> FEATURE:
<223> OTHER INFORMATION: Description of artificial sequence: Primer
<220> FEATURE:
<221> NAME/KEY: misc_feature
<222> LOCATION: (6)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u

<400> SEQUENCE: 61
aaygcngayt tgayggnga ygarat                                          26

<210> SEQ ID NO 62
<211> LENGTH: 26
<212> TYPE: DNA
<213> ORGANISM: Artificial sequence
<220> FEATURE:
<223> OTHER INFORMATION: Description of artificial sequence: Primer
<220> FEATURE:
<221> NAME/KEY: misc_feature
<222> LOCATION: (9)
<223> OTHER INFORMATION: n = a, g, c or t/u
<220> FEATURE:
<221> NAME/KEY: misc_feature
<222> LOCATION: (21)
<223> OTHER INFORMATION: n = a, g, c or t/u

<400> SEQUENCE: 62
atytsrtcnc crtcraartc ngcrtt                                         26

<210> SEQ ID NO 63
<211> LENGTH: 333
<212> TYPE: DNA
<213> ORGANISM: Lactobacillus reuteri

<400> SEQUENCE: 63
```

-continued

```
cttgttaagg aattacaagc attaggtctt gatatgaagg ttcttgatgg taacaacaag      60
gaaattcagt taaagaacat ggacgaagat gatgatgaag ttgtaaatgt tgatgcatta     120
gctaaatatg cagaagaaca taaaacagac gataagaaga acgaagaaga aaacaagtct     180
gaagcaactt caacaactac cgatgacaaa actaatcaaa attaatattt aggttgctac     240
ggtttactga agaaggagg aacatccttt gattgatgtc aataaatttg aaagtatgca     300
gatcggtctg gcatctccag ataagatccg tag                                  333
```

<210> SEQ ID NO 64
<211> LENGTH: 338
<212> TYPE: DNA
<213> ORGANISM: Bacillus subtilis

<400> SEQUENCE: 64

```
cttgttaagg aacttcaatc attaggtttg gatattcgtg ttcttgatat gaatcataat      60
gaaattgaac ttcgtgatat ggatgaagat tcaagtgaac acttaaacat tgattcattg     120
tcacgtatgg cagaagaaca agaaaagaag aagttagccg aagaaactgg aaaatcagaa     180
gataagaaag aaaacaagaa agatgcagat aagctagtag ctcctgcaga tgaatctgac     240
gacgaagttt ctaaatagta ggaggttaaa cttttgatcg acgtaaataa atttgaaagt     300
atgcaaattg gtcttgcatc acctaacaag atcagaag                             338
```

<210> SEQ ID NO 65
<211> LENGTH: 329
<212> TYPE: DNA
<213> ORGANISM: Lactobacillus gaseri

<400> SEQUENCE: 65

```
cttgttaagg aacttcaatc cttaggtttg gatattaaag tcttagatat ggaccacaag      60
gaaattgaat tacgtgacat ggatgatgat tctaatgatc acttcaacat tgacacttta     120
tctaagcttg ctgaacaaca agaaaagaag aagttagccg aagaagctgc aaagaaagat     180
gataagtcag ccgaacctgt agatcagagt gattcttcaa cttcatctga tgataaggtt     240
tctaagtaat aggaggttaa acttttgatc gacgtaaata agtttgaaag tatgcaaatt     300
ggtttggctt ctccaaacaa gatcagaag                                       329
```

<210> SEQ ID NO 66
<211> LENGTH: 296
<212> TYPE: DNA
<213> ORGANISM: Lactobacillus paracasei

<400> SEQUENCE: 66

```
cttgtcaaag aattgcaagc actgggtctg gatatgaagg tccttggcgc ggataaaaaa      60
gaaattgaac tgcgggacat ggacgacgac gaggatgata ttgtttctgt cgatgccttg     120
gcgaagtttg ctgctcagca ggaagaaaag aaggctcacg aagccgcagc acaagcaact     180
gacggtaagt ctgccaacag taccgacgat aagaaatagg aggttagccc tttgattgat     240
gtcaataagt ttgaaagtat gcaaatcggc ttagcctcgc cagataaaat ccgtag         296
```

<210> SEQ ID NO 67
<211> LENGTH: 386
<212> TYPE: DNA
<213> ORGANISM: Lactococcus lactis

<400> SEQUENCE: 67

```
ttggttaaag agttacaatc acttggtctt gatatgaaag tccttgatgc tgaccgtaat      60
gttcttgact tacgtgaatt ggatgaagat gaagtaatga ctcgtccaga taatacagaa     120
attactcctg aaatgcttga agcacaggaa gctattgttg cacaagcaga agctgaagaa     180
gaagctttga ttaacgctga tactgaaaaa taagattttg taattaatat tttgagatag     240
atttactgac aaaaatttct gtcagtaaat ctctaatctc ataatcgtct agcgttaaat     300
ttattagaag tggagaaaga attggttgat gtaaataaat ttgagagtat gcgtattggt     360
atcgcatctc cacaaaaaat tcgtta                                          386
```

```
<210> SEQ ID NO 68
<211> LENGTH: 344
<212> TYPE: DNA
<213> ORGANISM: Streptococcus pyogenes

<400> SEQUENCE: 68
cttgtaaaag aattgcaatc gcttggtctt gatatgcgtg tgcttgacga ggatgataat      60
gaagtggaac ttcgtgatct tgatgaaggt gaagacgatg acattatgca tgttgacgat     120
ctcgagaagg cacgtgaaaa acaagctcaa gaaactcaag aagtttctga acaactgac      180 gaaaaataag caatcaattc ttattaaata attatttact ggtctggggc aaaggcccca     240
ggaactggta agtcatcaa aggcagaaag gtaaaactag tggttgacgt aaatcgtttt      300
aaaagtatgc aaatcacatt agcctcacca gtaaggtcc gttc                       344
```

```
<210> SEQ ID NO 69
<211> LENGTH: 318
<212> TYPE: DNA
<213> ORGANISM: Lactobacillus helveticus

<400> SEQUENCE: 69
ttaatcaaag aacttcaaag cttaggtatg gatgtcaaaa tcctttctgg tgatgaagaa      60
gaaatagaaa tgagagattt agaagacgaa gaagatgcga acaagctga cggcctggca     120 ttatcaggtg atgaagagcc ggaagaaaca gcatctgcag acgttgaacg cgatgtagta     180
acaaaagaat aatctctagt tataaaggca agtgacatcg gttaatccga agataaaaag     240
ggaggtaggc cccttgctag atgtgaacaa ttttgagtat atgaacatcg gtcttgcttc     300
accagataaa atccgttc                                                   318
```

```
<210> SEQ ID NO 70
<211> LENGTH: 318
<212> TYPE: DNA
<213> ORGANISM: Bacillus subtilis

<400> SEQUENCE: 70
ttaatcaaag aacttcaaag cttaggtatg gatgtcaaaa tcctttctgg tgatgaagaa      60
gaaatagaaa tgagagattt agaagacgaa gaagatgcga acaagctga cggcctggca     120 ttatcaggtg atgaagagcc ggaagaaaca gcatctgcag acgttgaacg cgatgtagta     180
acaaaagaat aatctctagt tataaaggca agtgacatcg gttaatccga agataaaaag     240
ggaggtaggc cccttgctag atgtgaacaa ttttgagtat atgaacatcg gtcttgcttc     300
accagataaa atccgttc                                                   318
```

```
<210> SEQ ID NO 71
<211> LENGTH: 304
<212> TYPE: DNA
<213> ORGANISM: Bacillus halodurans
```

-continued

<400> SEQUENCE: 71

```
cttataaaag agctacagtc tctcggtatg gacgtcaaga tgctatcaag tactgaggaa     60
gagattgaaa tgaaagagct tgatgatgag gatgaacaag caagcgacaa attgaacttg    120
aatattgatt caacagaatc aaatgtttaa tcagctgaaa ggggagcagt cccctttcac    180
ttgctcttta aattcgttac ctgcttttgg acatggaaat cataagggag gttggcccct    240
tgatagacgt aaacaatttt gagtacatga aaattggtct tgcttcacca aataaaattc    300
gttc                                                                 304
```

<210> SEQ ID NO 72
<211> LENGTH: 363
<212> TYPE: DNA
<213> ORGANISM: Staphylococcus aureus

<400> SEQUENCE: 72

```
ttgatgaaag aattacaaag tttaggttta gatgtaaaag ttatggatga gcaagataat     60
gaaatcgaaa tgacagacgt tgatgacgat gatgttgtag aacgcaaagt agatttacaa    120
caaaatgatg ctcctgaaac acaaaaagaa gttactgatt aatacgcaat ttacaaaaca    180
ggcaaaaaga tactaagctg aattttattg atgattcagt ttagtacttt aagccatttt    240
aaataaatgc aaatcaatca aatagcacag ctaatctaaa ttgaaggagg taggctcctt    300
gattgatgta aataatttcc attatatgaa aataggattg gcttcacctg aaaaaatccg    360
ttc                                                                  363
```

<210> SEQ ID NO 73
<211> LENGTH: 352
<212> TYPE: DNA
<213> ORGANISM: Clostridium spiroforme

<400> SEQUENCE: 73

```
ttaaagaaag agttacaagc acttgcattg gatgtacgtt tgttagatga aaatgataat     60
gaagttgata tgcgtaatat tgaagaagag gaacatcgtt tcccgcgtag cattgataaa    120
gatgaagtaa ttgaaactcc aaaaactgat gatgaagttt ccgaagaaat tactgaagat    180
gatttaaatg tagaagaatg tgacgtatgt gaagaagata actttgagga caatgacttc    240
gaagacaatg atattgaaga aagtgaatca ttataggagg aattacgatg gcaaatacaa    300
ataaattctc agcgattcaa attggtttag cttcgcttca gaagattcgc ga            352
```

<210> SEQ ID NO 74
<211> LENGTH: 358
<212> TYPE: DNA
<213> ORGANISM: Clostridium leptum

<400> SEQUENCE: 74

```
ctcattaagg agcttcagtc cctgggcctg gatgtaaagg tgctggataa ggatgagcag     60
gagatcgacc taaagcagaa ctttgacgac gatgacgata tcggcttgaa cgacggcggc    120
accattctgg aggaggatga agtcatgacc tccatggatg gctacaccct ggaggacgat    180
ccggacgata acaacatgtt tgacgattcc ggctttttg acgaagacgg agacgatctt     240
ttggattttg attccattgc aagtgatatt cgtgaagaat aaggaggggc gataggatgg    300
agtttaacgt ttttgagtca attaaaatcg gactggcctc tccggataaa attcgaga      358
```

<210> SEQ ID NO 75

-continued

<211> LENGTH: 376
<212> TYPE: DNA
<213> ORGANISM: Clostridium nexile

<400> SEQUENCE: 75
ctcctgaaag aacttcagtc actgggactt gacgtgagag tattgcgtga agatcagaca 60
gaagttgaga ttatggagac aatcgattac ggtgaaacag atttacattc aattattgaa 120
ggagacagaa gatacaattc tgagaatgaa tcttatggag aacatggttt cagtcagcag 180
gaatttgcag gcgaggaact tgtggatgta gaggaagatg aatttgatga accggatgat 240
atcgattttg acgatatgtt agacgaagaa taggaggatt gccaataatg ccagtaacaa 300
ataatgaacc agcataccag ccgatgactt ttgatgcgat caaaatcggt ttggcgtcac 360
ctgaaaaaat cttgga 376

<210> SEQ ID NO 76
<211> LENGTH: 391
<212> TYPE: DNA
<213> ORGANISM: Ruminococcus hydrogenotrophicus

<400> SEQUENCE: 76
ctcttaaaag aacttcagtc cctgggtctg gacgtgagag tcctcaacga agaccagacc 60
gaggtggaga tcatggagag cgtggattac ggtgatacag atctgcactc catcattgag 120
ggagatcgtc atcgttcgca ggatgagtcc tacggagcaa tgggatatac gaagcaggaa 180
ttttccggtg aagagctggt agacatcgac gagagtgaag acgacagcga agacgaagat 240
gaagatttga ttgaattgga agattctctt gacagagaag agtagaaagg ggtaagaaac 300
aaatggcaga aatgaacaac aatgaaacct atcagccaat gactttcgat gccatcaaaa 360
tcggactggc gtcccctgag aaaatcagag a 391

<210> SEQ ID NO 77
<211> LENGTH: 182
<212> TYPE: DNA
<213> ORGANISM: Chlamydia muridarum

<400> SEQUENCE: 77
ttgattaaag aaatgcaagg tctagggctc gatgttcgcc ctatggtagt agatgcttaa 60
aaaacacttg ttggagataa gttaatgttc aaagaaggtt ctcgagacga tgcagcccta 120
gcaaaagaag ggttgtttga taagttagaa attgggattg cttcagatgt gactattcgc 180
ga 182

<210> SEQ ID NO 78
<211> LENGTH: 182
<212> TYPE: DNA
<213> ORGANISM: Chlamydia trachomatis

<400> SEQUENCE: 78
ttgattaaag aaatgcaagg tctagggctt gatgttcgcc ctatggtagt agatgcttaa 60
aaaacacttg ttggagagaa gttaatgttc agagaaggtt ctcgagacga tgcagccctg 120
gtaaaagaag ggctgtttga taagttagaa attgggattg cttcagatgt gactattcgc 180
ga 182

<210> SEQ ID NO 79
<211> LENGTH: 181
<212> TYPE: DNA
<213> ORGANISM: Chlamydophila pneumoniae

<400> SEQUENCE: 79

```
ctaattaaag agatgcaggg tctaggactt gatgttcgtc ctatggtcgt agacgcttaa      60
aaaatgacgt tttggagaaa ataatgttcg gagaaaattc tcgagacatt ggagttcttt     120
ctaaagaagg actatttgat aaattagaga taggcatagc ttcagatatt acaattcgtg     180
a                                                                     181
```

<210> SEQ ID NO 80
<211> LENGTH: 181
<212> TYPE: DNA
<213> ORGANISM: Chlamydophila pneumoniae

<400> SEQUENCE: 80

```
ctaattaaag agatgcaggg tctaggactt gatgttcgtc ctatggtcgt agacgcttaa      60
aaaatgacgt tttggagaaa ataatgttcg gagaaaattc tcgagacatt ggagttcttt     120
ctaaagaagg actatttgat aaattagaga taggcatagc ttcagatatt acaattcgtg     180
a                                                                     181
```

<210> SEQ ID NO 81
<211> LENGTH: 181
<212> TYPE: DNA
<213> ORGANISM: Chlamydophila pneumoniae

<400> SEQUENCE: 81

```
ctaattaaag agatgcaggg tctaggactt gatgttcgtc ctatggtcgt agacgcttaa      60
aaaatgacgt tttggagaaa ataatgttcg gagaaaattc tcgagacatt ggagttcttt     120
ctaaagaagg actatttgat aaattagaga taggcatagc ttcagatatt acaattcgtg     180
a                                                                     181
```

<210> SEQ ID NO 82
<211> LENGTH: 225
<212> TYPE: DNA
<213> ORGANISM: Klebsiella pneumoniae

<400> SEQUENCE: 82

```
ttgttgaaag agattcgttc gctgggtatc aacatcgaac tggaagacga gtaattctcg      60
ctcaaacagg tcactgctgt cgggttaaaa cccggcagcg gattgtgcta actccgacgg     120
gagcaaatcc gtgaaagatt tattaaagtt tctgaaagcg cagactaaaa ccgaagagtt     180
tgatgcgatc aaaattgctc tggcttcgcc agacatgatc cgttc                     225
```

<210> SEQ ID NO 83
<211> LENGTH: 225
<212> TYPE: DNA
<213> ORGANISM: Escherichia coli

<400> SEQUENCE: 83

```
ttgttgaaag agattcgttc gctgggtatc aacatcgaac tggaagacga gtaattctcg      60
ctcaaacagg tcactgctgt cgggttaaaa cccggcagcg gattgtgcta actccgacgg     120
gagcaaatcc gtgaaagatt tattaaagtt tctgaaagcg cagactaaaa ccgaagagtt     180
tgatgcgatc aaaattgctc tggcttcgcc agacatgatc cgttc                     225
```

<210> SEQ ID NO 84
<211> LENGTH: 225
<212> TYPE: DNA

<210> SEQ ID NO 84
<211> LENGTH: 225
<212> TYPE: DNA
<213> ORGANISM: Escherichia coli

<400> SEQUENCE: 84

```
ttgttgaaag agattcgttc gctgggtatc aacatcgaac tggaagacga gtaattctcg      60
ctcaaacagg tcactgctgt cggggtaaaa cccggcagcg gattgtgcta actccgacgg     120
gagcaaatcc gtgaaagatt tattaaagtt tctgaaagcg cagactaaaa ccgaagagtt     180
tgatgcgatc aaaattgctc tggcttcgcc agacatgatc cgttc                    225
```

<210> SEQ ID NO 85
<211> LENGTH: 225
<212> TYPE: DNA
<213> ORGANISM: Escherichia coli

<400> SEQUENCE: 85

```
ttgttgaaag agattcgttc gctgggtatc aacatcgaac tggaagacga gtaattctcg      60
ctcaaacagg tcactgctgt cggggtaaaa cccggcagcg gattgtgcta actccgacgg     120
gagcaaatcc gtgaaagatt tattaaagtt tctgaaagcg cagactaaaa ccgaagagtt     180
tgatgcgatc aaaattgctc tggcttcgcc agacatgatc cgttc                    225
```

<210> SEQ ID NO 86
<211> LENGTH: 225
<212> TYPE: DNA
<213> ORGANISM: Escherichia coli

<400> SEQUENCE: 86

```
ttgttgaaag agattcgttc gctgggtatc aacatcgaac tggaagacga gtaattctcg      60
ctcaaacagg tcactgctgt cggggtaaaa cccggcagcg gattgtgcta actccgacgg     120
gagcaaatcc gtgaaagatt tattaaagtt tctgaaagcg cagactaaaa ccgaagagtt     180
tgatgcgatc aaaattgctc tggcttcgcc agacatgatc cgttc                    225
```

<210> SEQ ID NO 87
<211> LENGTH: 225
<212> TYPE: DNA
<213> ORGANISM: Salmonella typhimurium

<400> SEQUENCE: 87

```
ctgttgaaag agatccgctc gctgggcatc aacatcgaac tggaagacga gtaattctcg      60
ctcaaacagg tcactggtgt cggggtaaaa cccgacacca gattgtgcta actccgacgg     120
gagcaaatcc gtgaaagatt tattaaagtt tctgaaagcg cagactaaaa ccgaagagtt     180
tgatgcgatc aaaattgctc tggcttcgcc agacatgatc cgttc                    225
```

<210> SEQ ID NO 88
<211> LENGTH: 225
<212> TYPE: DNA
<213> ORGANISM: Enterobacter cloacae

<400> SEQUENCE: 88

```
ctgttgaaag agattcgttc gctgggtatc aacatcgaac tggaagacga gtaattctcg      60
ctcaaacagg tcactggtgc cgggttaacc cccggcaccg gattgtgcta actccgacgg     120
gagcaaatcc gtgaaagatt tattaaagtt tctgaaagcg cagactaaaa ccgaagagtt     180
tgatgcgatc aaaattgctc tggcttcgcc agacatgatc cgttc                    225
```

<210> SEQ ID NO 89
<211> LENGTH: 225

```
<212> TYPE: DNA
<213> ORGANISM: Citrobacter freundii

<400> SEQUENCE: 89
ctgttgaaag agattcgttc gctgggtatc aacatcgagc tggaagacga gtaactctcg      60
atcaaacagg tcactggtgc tggcgtaata gccagcgcca gattgtgcta actccgacgg     120
gagcaaatcc gtgaaagatt tattaaagtt tctgaaagcg cagactaaaa ccgaagagtt     180
tgatgcgatc aaaattgcgc tggcctcgcc agacatgatc cgttc                    225

<210> SEQ ID NO 90
<211> LENGTH: 225
<212> TYPE: DNA
<213> ORGANISM: Klebsiella oxytoca

<400> SEQUENCE: 90
ttgttgaaag agattcgctc gctgggcatc aacatcgaac tggaagacga gtaactctcg      60
ctcaaacagg tcactggtgc cggggtaaga cccggcgcca gattgtgcta actccgacgg     120
gagcaaatcc gtgaaagact tattaaagtt tctgaaagcg caaactaaaa ccgaagagtt     180
tgatgcgatc aaaattgctc tggcatcgcc agacatgatc cgttc                    225

<210> SEQ ID NO 91
<211> LENGTH: 267
<212> TYPE: DNA
<213> ORGANISM: Serratia liquefaciens

<400> SEQUENCE: 91
ctgttgaaag aaatccgctc gctcggtatc aacatcgaac tggaagacga gtaatcgttt      60
ttccagctca ggctcccggc cttagggagc ctgagggtgg ttgttcaggt cacacgggtg     120
cgcgatttgt cagcgtgcac ccaacaggtt taactccgac aggagccaat ccgtgaaaga     180
cttattgaag tttctgaaag cgcaaactaa gaccgaagag tttgatgcga tcaagattgc     240
tctggcatcg ccagacatga tccgttc                                         267

<210> SEQ ID NO 92
<211> LENGTH: 267
<212> TYPE: DNA
<213> ORGANISM: Serratia marcescens

<400> SEQUENCE: 92
ctgttgaaag aaatccgctc gctcggcatc aacatcgaac tggaagacga gtaatcgtca      60
tgccggctca ggctccccgc ctaagggagc ctgagggtgg ttgttcaggt cacacgggta     120
cctactgcgg ttgtgggtac ccaacaggtt taactccgac aggagccaat ccgtgaaaga     180
cttattgaag tttctgaaag cgcaaactaa gaccgaagag tttgatgcga tcaagattgc     240
tctggcctcg ccagacatga tccgttc                                         267

<210> SEQ ID NO 93
<211> LENGTH: 257
<212> TYPE: DNA
<213> ORGANISM: Morganella morganii

<400> SEQUENCE: 93
ttgctgaaag aaatccgttc cctcggtatc aatatcgagc tggaagacga gtaattaccg      60
ttgtggctgc ccgtggtaca cgggcagcac cagtaaatct ggtttaaggg acaaacagac     120
gaccgtttgt ctcacaggtc taactccgac aggagccatt tcgtgaaaga cttattaaag     180
```

```
tttctgaaag cgcaaaccaa gaccgaagag tttgatgcga tcaaaattgg tctggcctca    240
cctgacatga ttcgttc                                                   257

<210> SEQ ID NO 94
<211> LENGTH: 271
<212> TYPE: DNA
<213> ORGANISM: Proteus mirabilis

<400> SEQUENCE: 94
ttgttgaaag agatccgttc actgggtatc aacatcgaat tggaagacga ataacgtatt    60
ccatgaaagc agactgctaa atatggcagt ctgctaaaca gtgactacac tggtttaaag   120
gggtgaatga caggggtcat ttgcctggca ggtctaactc cgacaggagc catttcgtga   180
aagacttatt aaagtttctg aaagcgcaaa ccaagaccga agagtttgat gcgatcaaaa   240
ttgctctggc atcacctgat atgatccgtt c                                   271

<210> SEQ ID NO 95
<211> LENGTH: 253
<212> TYPE: DNA
<213> ORGANISM: VIBRIO CHOLERAE

<400> SEQUENCE: 95
ctgttgaaag agattcgctc gctgggtatc aacatcgagc tagaagacga ataataaacc    60
ctaaggtttc cccgcaaggg gaagcctacc ggtttcggta ggaaggtgct cgttgccaat   120
cgcagcgagt tccttttaac tccttacagg agctgaatgt gaaagactta ttaaactttc   180
taaaagcaca gcataagacc gaagaatttg atgcgatcaa aatcggtctg gcttcaccag   240
acatgatccg ttc                                                       253

<210> SEQ ID NO 96
<211> LENGTH: 214
<212> TYPE: DNA
<213> ORGANISM: Pseudomonas aeruginosa

<400> SEQUENCE: 96
ctgatcaaag agatccgttc gctcggcatc gacatcgaac tggaaaccga ataacacgtg    60
acgctagacg gtgcggctgg tcaaggccgg tcgcaccggg tccgtgagga ggaaaggcct   120
tgaaagactt gcttaatctg ttgaaaaacc agggtcaaat cgaagagttc gatgccatcc   180
gtattggcct ggcttcgccc gagatgattc gttc                                214

<210> SEQ ID NO 97
<211> LENGTH: 214
<212> TYPE: DNA
<213> ORGANISM: Pseudomonas aeruginosa

<400> SEQUENCE: 97
ctgatcaaag agatccgttc gctcggcatc gacatcgaac tggaaaccga ataacacgtg    60
acgctagacg gtgcggctgg tcaaggccgg tcgcaccggg tccgtgagga ggaaaggcct   120
tgaaagactt gcttaatctg ttgaaaaacc agggtcaaat cgaagagttc gatgccatcc   180
gtattggcct ggcttcgccc gagatgattc gttc                                214

<210> SEQ ID NO 98
<211> LENGTH: 212
<212> TYPE: DNA
<213> ORGANISM: Pseudomonas putida

<400> SEQUENCE: 98
```

-continued

```
ttgatcaaag agatccgttc gctcggtatc gatatcgatc tggaaaccga ataacacgtg      60
acgcgaaggg gagtggggca ggtaatgctg ctccctgctc cgccaggagg aaaggccttg     120
aaagacctac tgattttgct gaaaaaccag ggtcaagtcg aagagttcga cgccatccgc     180
atcggtctgg cgtcgcctga atgatccgt tc                                    212
```

<210> SEQ ID NO 99
<211> LENGTH: 228
<212> TYPE: DNA
<213> ORGANISM: Shewanella violacea

<400> SEQUENCE: 99

```
ttgttgaagg aaatccgttc actcggtatt aatatcgagt tggatcaaga ctaaaattaa      60
cttaggttaa tttggcaata aattggtgtc ctgcattagc ggggcacccg gtttactcct     120
tcaggagaga aacgtgaaag acttattaaa gtttctgaaa cagcaaagca agaccgaaga     180
atttaacggt atcaagatcg gactagcgtc accagatctg atccgctc                  228
```

<210> SEQ ID NO 100
<211> LENGTH: 393
<212> TYPE: DNA
<213> ORGANISM: Haemophilus influenzae

<400> SEQUENCE: 100

```
attatgaaag aaatccgctc acttggttta aatatcgagt tagacgaaga gtaatcactg      60
attactataa atggtgctga tcccttggct ccacccgttt acggggagc tggcgcgaag     120 actgaggggg gatttatatc ctaagccccc ttccgccctt cgggcacctt ccctcgcaaa     180
gcaggggaag gcaagaggaa caacaacata agatttgaaa tcgccgaagt gcggtcaaaa     240
ttctccgaaa tttttaaccg cactttaaac ctttaactcc gacaggagaa catttgtgaa     300
agacttagtt aagttttttaa aagcacaatc aaaaaccagt gaagattttg atgtgattaa     360
aattgggtta gcttccccag atatgatccg ttc                                  393
```

<210> SEQ ID NO 101
<211> LENGTH: 262
<212> TYPE: DNA
<213> ORGANISM: Pasteurella multocida

<400> SEQUENCE: 101

```
attatgaaag aaattcgctc gcttggtatc aatattgatt tagatgaaga ttaatctgac      60
atcataacca agcttggtgt aaagcaatgt acgcgcaagt gcggtaaaaa tttttaaaat     120 tcagccgca cttgaataag tttaactccg acaggagcaa atctgtgaaa gacttagtta     180 agttttttaaa agcacaatca aaaacaagtg aagattttga tgtgatcaaa attggtttag     240
cctcaccgga catgatccgt tc                                              262
```

<210> SEQ ID NO 102
<211> LENGTH: 306
<212> TYPE: DNA
<213> ORGANISM: Neisseria meningitidis

<400> SEQUENCE: 102

```
ttggtcaaag agattcgctc actgggcttg gatatcgatt tggaacgcta ctgatacggg      60
tttcagacgg cataagggga gctgttctgc aggtatgcgg ggcagccgac aatgttttaaa     120 aacgaaatgc cgtctgaaaa cactgtacct ctatccatat cgaaaatccg ccatgcggta     180
```

```
aaaatacttc cttcaaggag caaaaatgaa tttgttgaac ttatttaatc cgttgcaaac      240
tgccggcatg gaagaagagt ttgatgccat caaaatcggt attgcctctc ccgaaaccat      300
ccgctc                                                                306
```

<210> SEQ ID NO 103
<211> LENGTH: 311
<212> TYPE: DNA
<213> ORGANISM: Neisseria meningitidis

<400> SEQUENCE: 103

```
ttggtcaaag agattcgctc actgggcttg gatatcgatt tggaacgtta ctaaacaaaa      60
gttttcagac ggcctttcag ggtcgtctga aaagtggtt tcagaataag aatgaagcaa       120
tcggcattta ggccgtctga aatcaaaagt accgtttccc aatatcgaaa atccgccatg      180
cggtaaaaat acttccttca aggagcaaaa atgaatttgt tgaacttatt taatccgttg      240
caaactgccg gcatggaaga agagtttgat gccattaaaa tcgtattgc ctctcccgaa       300 accatccgct c                                                          311
```

<210> SEQ ID NO 104
<211> LENGTH: 226
<212> TYPE: DNA
<213> ORGANISM: Buchnera sp

<400> SEQUENCE: 104

```
cttttaaaag aaattcggtc attagggatt aatattgaac tagaaagcga ataacaaaat      60
tagcaatatt ataaaaatat ttatgtatta tttatttacc ttaaaagttt tactccaacg      120
agagctaacg tgtgaaagat ttactaaaat ttctaaaatc ccaaactaaa atgaagatt       180 ttgatgctat taaaatctcg ttagcttcac ctgatatgat cagatc                    226
```

<210> SEQ ID NO 105
<211> LENGTH: 247
<212> TYPE: DNA
<213> ORGANISM: Xylella fastidiosa

<400> SEQUENCE: 105

```
ctcgtgaaag aaatccgctc cttagcaatt aatattgagt tggaagataa ctaagatgcg      60
ttgttatgga ttaattcatc tgtttggagg cccagagctc cattgtcctc tgtttccaac      120
tcgtcccgat gcccgaattt cggagaagaa gtatgaaaga tctactcaat cttttttaatc    180 agcagcgcca gacattggat ttcgatgcca tcaagattgg ccttgcctcg cctgccttga     240
ttagatc                                                               247
```

<210> SEQ ID NO 106
<211> LENGTH: 265
<212> TYPE: DNA
<213> ORGANISM: Caulobacter crescentus

<400> SEQUENCE: 106

```
ctggtcaagg aaatgcgctc gctcggcctg aacgtcgagc tggagaacag ctgatctgga      60
tctccctcct cgcctgcccc tcttaggaag ggtggccggg gaggggcctc ctttcagccc     120
gctctcccct caagaattttc gcgggaaacc ccgcagaagg aaccaagatg aaccaggaag    180
tcctgaacat cttcaatccg gtccaggccg ctccgacctt cgaccagatc cgtatctcgc    240
tcgcctcgcc ggaaaagatc cgctc                                           265
```

<210> SEQ ID NO 107
<211> LENGTH: 325
<212> TYPE: DNA
<213> ORGANISM: Mezorhizobium loti

<400> SEQUENCE: 107

```
ctcgtcaagg aaatgcggtc tctcggcctc aatgtcgagc tggagaacac caagctcgac      60
gacgcccctg tccggctgcc cgacgcggcc gagtaaaggc tacagcgcgc cgcacgaagt     120
tgcggcgcgc aaaggaattc gacggccggt ggccgacaaa agatggcggg cgtttggccc     180
gcgactagat gcaaggggtt ttcgaggacc ccgaaaagga gaacggcatg aaccaagagg     240
tcatgaatct cttcaatccg caggcgcctg cgcaggtgtt cgattccatc cggatctcac     300
tggccagccc tgagaagatt ctgtc                                           325
```

<210> SEQ ID NO 108
<211> LENGTH: 311
<212> TYPE: DNA
<213> ORGANISM: Rickettsia prowasekii

<400> SEQUENCE: 108

```
atgataaaag aatttagatc tttatgtctc aacgtaaagc ttgaagtaac tccaagtaaa      60
taaagtgtat atatgttgta cataatttgt cttgttgtat aatttaaaaa ttgttattgc     120
aagccaaact aaatgaatgt agtgagccat aatgttattt tgtatttaag ctatggagta     180
acatttttaga gtaggagtaa tttttaggga aaagtattta tgagcgtagt taattttttat     240
ggacaattaa gtaatactca acaatttgac cagataagga ttaatatagc cagtcctgat     300
caggtacgtt c                                                           311
```

<210> SEQ ID NO 109
<211> LENGTH: 188
<212> TYPE: DNA
<213> ORGANISM: Borrelia burgdorferi

<400> SEQUENCE: 109

```
ctaatgcaag agcttagagg gcttggactt gatttgtcaa tttatgatga tgctgggaat      60
caggttcctt tgacagaaaa agaagaagaa ttgattaata aaagctaggt ttttggagtt     120
tttatgaaag agataaaaga ttttgaaaga ataaaaatta aatagcgtc tcccgatcaa      180
attagaaa                                                               188
```

<210> SEQ ID NO 110
<211> LENGTH: 197
<212> TYPE: DNA
<213> ORGANISM: Treponema pallidum

<400> SEQUENCE: 110

```
ttggtgcagg agctgcgggg acttgcgctc gactttacga tttacgatgc gaagggcaag      60
cagattccgc tcactgagcg cgatgaagaa atgacgaata agattggctc taaattttaa     120
ggggtgcagg gaatgaagga tatccgggat tttgacagtt tacagataaa gcttgcctcc     180
cctgatacca ttcgggc                                                    197
```

<210> SEQ ID NO 111
<211> LENGTH: 159
<212> TYPE: DNA
<213> ORGANISM: Campylobacter jejuni

<400> SEQUENCE: 111

```
ttaaccaatg agcttaaatc tcttgcttta gatgttgaga ttttttgataa ggatgaagat      60 aatgagtaaa tttaaagtaa tagaaattaa agaagatgca agacctagag attttgaagc     120
atttcaacta agacttgcaa gtcctgaaaa aatcaaatc                            159
```

```
<210> SEQ ID NO 112
<211> LENGTH: 161
<212> TYPE: DNA
<213> ORGANISM: Helicobacter pylori

<400> SEQUENCE: 112
ttgactaaag aattgcaatc gctcgctttg gatattaata ttttttgggga cgatgtggat     60 gaggatggag cacctaaacc cattgtcatt aaagaagatg acaggcctaa agactttagc    120
tctttccagc tcacactagc tagccctgaa aaaatccatt c                        161
```

```
<210> SEQ ID NO 113
<211> LENGTH: 161
<212> TYPE: DNA
<213> ORGANISM: Helicobacter pylori

<400> SEQUENCE: 113
ttgactaaag aattgcagtc gctcgctttg gatattaata ttttttgggga cgatgtggat     60 gaagatggag cgcctagacc cattatgatc aaagaagatg acaggcctaa agactttagc    120
tctttccagc tcactctagc tagccctgaa aagatccatt c                        161
```

```
<210> SEQ ID NO 114
<211> LENGTH: 175
<212> TYPE: DNA
<213> ORGANISM: Aquifex aeolicus

<400> SEQUENCE: 114
ctcgtaagag agctaaaggc tcttgggcta aacgttaagt gtctgaatgg tgaagagaag      60
ccttgtgacg aggttgaagt taaagaggag gaagaaaaat gagtgaagca agaagggta    120 tcttccccctt ctcaaaaatt aaattgatgc tcgcttctcc cgaggatatc agaag         175
```

```
<210> SEQ ID NO 115
<211> LENGTH: 175
<212> TYPE: DNA
<213> ORGANISM: Aquifex pyrophilus

<400> SEQUENCE: 115
ctcgttaggg agctcaaagg tctcagcctt aacgttaagt gtatgaacgg tgaggagaag      60
ccctgtgacc aagttgagat taaagaggag gaagaaaaat gagcacaaaa ggtagggta    120 tctttccttt ctcaaaaatt aagcttatgc tcgcttctcc cgacgatatc agaag          175
```

```
<210> SEQ ID NO 116
<211> LENGTH: 293
<212> TYPE: DNA
<213> ORGANISM: Deinococcus radiodurans

<400> SEQUENCE: 116
ctggtcaagg aactccactc gctcggtctg gacgtcgagg tgctcgacca cggcgacaag      60
gccgtggaca tctttgaagg gatgatgccc aagcgctaag gcgcctgcgg cactgccaac    120
ccgtcgagca ctgtcaaacc gtctaaaggt caaaccgcca acatctttca gccgttcgac    180
ggtgagacag ttcgacggtt tgaccaacaa aagagcctcc attccacagg agcctgaatg    240
aaagacttca acaaagtccg catcgccatc gccagcccgg agaagatccg cga            293
```

<210> SEQ ID NO 117
<211> LENGTH: 177
<212> TYPE: DNA
<213> ORGANISM: Thermus aquaticus

<400> SEQUENCE: 117

| | | | | | |
|---|---|---|---|---|---|
| ctggtgaagg | agcttcaggc | cctggccctg | gacgtgcaga | ccctggacga | gaaggacaac | 60 |
| cccgtggaca | tttttgaggg | cctggcctcc | aagaggtgag | cccttttctg | gaggaaagat | 120 |
| gaaaaaggaa | gtccgcaagg | tccgcatcgc | cctggcctcc | cccgagaaga | tccgctc | 177 |

<210> SEQ ID NO 118
<211> LENGTH: 174
<212> TYPE: DNA
<213> ORGANISM: Thermotoga maritima

<400> SEQUENCE: 118

| | | | | | |
|---|---|---|---|---|---|
| ctcatcaaag | aactcagagg | tctcgcgctc | gatgtgagac | tctacgatga | gaacggtaac | 60 |
| gagatagata | tcgacaagta | ctgattggga | ggttggtaga | atgccaatgt | cctctttcaa | 120 |
| gaggaagata | aaggcaattc | agataaagat | agcctctccg | gaagtgataa | gaag | 174 |

<210> SEQ ID NO 119
<211> LENGTH: 324
<212> TYPE: DNA
<213> ORGANISM: Streptomyces coelicolor

<400> SEQUENCE: 119

| | | | | | |
|---|---|---|---|---|---|
| ctcatcaagg | agatgcagtc | cctgtgcctc | aacgtggagg | tgctgtcctc | ggacggcatg | 60 |
| tccatcgaga | tgcgtgacac | cgacgaggac | gtcttccgcg | cagcggagga | gctcggcatc | 120 |
| gacctgtcgc | ggcgcgagcc | gagcagcgtc | gaagaggtct | gacgggagtc | aggcggggcc | 180 |
| tgtcctccac | aggccccgcc | gatcccgcga | ccccgtttc | agaccacaga | cttacaaccc | 240 |
| tgagagggat | tgacgcatag | tgctcgacgt | caacttcttc | gacgagctcc | ggatcggtct | 300 |
| ggccaccgct | gacgacatcc | gtca | | | | 324 |

<210> SEQ ID NO 120
<211> LENGTH: 281
<212> TYPE: DNA
<213> ORGANISM: Mycobacterium leprae

<400> SEQUENCE: 120

| | | | | | |
|---|---|---|---|---|---|
| ctgctcaagg | agttacagtc | gctgtgtctc | aacgtcgagg | tgctgtcgtc | cgacggtgcg | 60 |
| gcgatcgagt | tgcgcgaagg | tgaggatgag | gacctcgagc | gggctgcggc | caacctcggt | 120 |
| atcaacttgt | cccgcaacga | atcggcgtcc | atagaagatc | tggcttagcg | aacttggcat | 180 |
| tatcgtcact | aaacccgcaa | ggggaaaggg | agttacgtgc | tagacgtcaa | cttcttcgat | 240 |
| gaactccgca | ttggcctggc | taccgcggag | gacattcgtc | a | | 281 |

<210> SEQ ID NO 121
<211> LENGTH: 277
<212> TYPE: DNA
<213> ORGANISM: Mycobacterium tuberculosis

<400> SEQUENCE: 121

| | | | | | |
|---|---|---|---|---|---|
| ctgctcaaag | aactgcagtc | gctgtgcctc | aacgtcgagg | tgctatcgag | tgacggtgcg | 60 |
| gcgatcgaac | tgcgcgaagg | tgaggacgag | gacctggagc | gggccgcggc | caacctggga | 120 |

| atcaatctgt cccgcaacga atccgcaagt gtcgaggatc ttgcgtaaag ctgtcgcaaa | 180 |
| attactaaac ccgttagggg aaagggagtt acgtgctcga cgtcaacttc ttcgatgaac | 240 |
| tccgcatcgg tcttgctacc gcggaggaca tcaggca | 277 |

<210> SEQ ID NO 122
<211> LENGTH: 277
<212> TYPE: DNA
<213> ORGANISM: Mycobacterium tuberculosis

<400> SEQUENCE: 122

| ctgctcaaag aactgcagtc gctgtgcctc aacgtcgagg tgctatcgag tgacggtgcg | 60 |
| gcgatcgaac tgcgcgaagg tgaggacgag gacctggagc gggccgcggc caacctggga | 120 |
| atcaatctgt cccgcaacga atccgcaagt gtcgaggatc ttgcgtaaag ctgtcgcaaa | 180 |
| attactaaac ccgttagggg aaagggagtt acgtgctcga cgtcaacttc ttcgatgaac | 240 |
| tccgcatcgg tcttgctacc gcggaggaca tcaggca | 277 |

<210> SEQ ID NO 123
<211> LENGTH: 192
<212> TYPE: DNA
<213> ORGANISM: Porphyromonas cangingivalis

<400> SEQUENCE: 123

| ctcctacacg agctcaaagg tcttggtcta agcttctgta tggagtaata ggcgaggata | 60 |
| tgtgattata gttttttcct catcagaata aatctcccat tatatagtta tggcattcaa | 120 |
| aagagataca aagataaagg ccaacttcac ccgtattaag atcggtatcg cttctcccga | 180 |
| agaggtattg ga | 192 |

<210> SEQ ID NO 124
<211> LENGTH: 257
<212> TYPE: DNA
<213> ORGANISM: Mycoplasma genitalium

<400> SEQUENCE: 124

| ttgacaaaag aattacaggg cttggcttta tctgtttcat ttatctatga tgacaacacc | 60 |
| caacaagact ccaataatgt ttccatcttg caaagtgatg gggaacaaga tgaatttttc | 120 |
| aatgattttg aatttgacac tgagggttat tagaaattaa caatgacaac aacaagacgt | 180 |
| aataaaagaa ataacaagct ttataaaaac attaaagcaa ttaaactttc catcgcttcc | 240 |
| aatgacacca ttttgaa | 257 |

<210> SEQ ID NO 125
<211> LENGTH: 245
<212> TYPE: DNA
<213> ORGANISM: Mycoplasma pneumoniae

<400> SEQUENCE: 125

| ttaacgaagg aactacaagg gttagcgttg agtgtgtcct ttatttacga tgacaacacc | 60 |
| caacaagatt ccaacaacgt ttcaattctc caagctgatg gagaacagga cgatctcttt | 120 |
| aatgactttg aatttgacac ggagggttat taattaatga caaagcgtaa taaaaagaac | 180 |
| aacaagctgt acaagaacat taaggcaatt aagctttcga ttgcttccaa cgacacgatc | 240 |
| ctaaa | 245 |

<210> SEQ ID NO 126
<211> LENGTH: 305

<212> TYPE: DNA
<213> ORGANISM: Ureaplasma urealyticum

<400> SEQUENCE: 126

```
ttaacaaaac aaatgcaagg tttagggtta tgtattaccg ttgaaacaaa agatgatcgt      60
atggtagata ttaatgaata tacactaaat caaaatcgtt taaataatga cgatgatgag     120
gttattttag atgaaaatct aaaagagatc aatgattcta atgaagaaat atttaataca     180
aactttaata ataatgacta tgatgatgaa gagaacttct aaataataga aggtaaaat      240
aatatgagtc aaaagggat taaatcatta acgatttcca ttgcttcacc tgaacaaatt     300
ttaaa                                                                 305
```

<210> SEQ ID NO 127
<211> LENGTH: 244
<212> TYPE: DNA
<213> ORGANISM: Mycoplasma pulmonis

<400> SEQUENCE: 127

```
ttagcctatg aattaagagg gctaggaatc aaacttcaaa ttcatgaaaa agaagaagaa      60
aaacaagaac taccaagcca agaatatgaa agtttaaatc ttgatcaaga gctaaaaaca     120
gcttctgaaa atgttagtga aagtgagttt taattatgcc aaaaactaga aaatattcaa     180
cagttgatga agaaaagatt ttaaaagtta gcttatctct tgcaactaaa gaagatgttt     240
taga                                                                  244
```

<210> SEQ ID NO 128
<211> LENGTH: 202
<212> TYPE: DNA
<213> ORGANISM: Plasmodium falciparum

<400> SEQUENCE: 128

```
attttaaaag agttacaaag tttagctatt aatatagaag cttttttgtat atttaatgat      60
acaaataatt tattagaaaa tttacctatt aatataattt attaataatg ataatacata     120
ataatataaa ttttatagga ttaaaattaa atatattaaa tcctaaacaa ataataaaat     180
ggtcttcaat attttataaa aa                                              202
```

<210> SEQ ID NO 129
<211> LENGTH: 136
<212> TYPE: DNA
<213> ORGANISM: Archaeoglobus fulgidus

<400> SEQUENCE: 129

```
cttctggatg agctgaagtc aatgatgatc gctccgagaa taattctcgg agataaggca      60
tgaggtgaaa tgagatggta ccgaagagga tttcagccat taaatttgag gttctctccc     120
cccaagagat aagaag                                                     136
```

<210> SEQ ID NO 130
<211> LENGTH: 169
<212> TYPE: DNA
<213> ORGANISM: Methanothermobacter thermoautotrophicus

<400> SEQUENCE: 130

```
ttacttctcg aactcaagag tctctgtatc ttcccgaaac tcatactgga agataaggca      60
tgataatgga tttaagggaa taacaaaaag gagagaatac cttgagagga attttaaaga     120
aaatttccca gataaacttt ggcctcatgt cccccgagga tatcaggaa                 169
```

<210> SEQ ID NO 131
<211> LENGTH: 136
<212> TYPE: DNA
<213> ORGANISM: Halobacterium sp

<400> SEQUENCE: 131
ctactcgacg agatgaaggc gctcggcatc gcgccgcgcc tggaactgga ggaggcagtg      60
taatgagtgc aggacaagcc cccaaggaaa tcggcgaaat cagcttcggg ctgatggacc    120
cagaggagta ccgcga                                                    136

<210> SEQ ID NO 132
<211> LENGTH: 127
<212> TYPE: DNA
<213> ORGANISM: Thermoplasma volcanium

<400> SEQUENCE: 132
atgagggatg agctgatatc tctcggtgtt gttatgcgtc ttatgttggg tgatatgaaa      60
tgatgggaat ttctaaaaga atttcaagta ttaaatttgc gcttctttct ccagacgaga    120
taagaaa                                                              127

<210> SEQ ID NO 133
<211> LENGTH: 127
<212> TYPE: DNA
<213> ORGANISM: Thermoplasma acidophilum

<400> SEQUENCE: 133
atgagggatg agctgatctc tctcggtgtt gttatgaggt taatgctcgg tgatatgaaa      60
tgatgggaat atcaaaaaga atttcatcaa taaaatttgc ccttctttct ccggatgaga    120
taagaaa                                                              127

<210> SEQ ID NO 134
<211> LENGTH: 141
<212> TYPE: DNA
<213> ORGANISM: Sulfolobus acidocaldarius

<400> SEQUENCE: 134
ttaattcaag aacttatgag tatggtaatt tcaccgagat taattttagg tgaaaaagta      60
aacttaggag gtgcttcaaa tgagtgagaa gattatacgg ggcgtaaaat ttggtgtatt    120
atcacctaat gaaataaggc a                                              141

<210> SEQ ID NO 135
<211> LENGTH: 145
<212> TYPE: DNA
<213> ORGANISM: Sulfolobus solfataricus

<400> SEQUENCE: 135
ttaattcaag aactaatgag tatgattatc tcacctaggt tagttttgga ggataaagtt      60
ggattaagtg gaggttaagg gaaatgagtg aaaagaatat aaaaggaata agtttggaa    120 tactttctcc tgacgaaata agaaa                                          145

<210> SEQ ID NO 136
<211> LENGTH: 134
<212> TYPE: DNA
<213> ORGANISM: Pyrococcus abyssi

<400> SEQUENCE: 136
ctcttggatg agcttaaggc catggttatt aggccaaagt taaacctcac ggagagggtg      60

```
tgagctatgc aatccgttaa gaaggttatc ggtagtatag agtttggaat tctctcccct    120
caagaaatta gaaa                                                      134
```

<210> SEQ ID NO 137
<211> LENGTH: 134
<212> TYPE: DNA
<213> ORGANISM: Pyrococcus horikoshii

<400> SEQUENCE: 137

```
cttctggatg agcttaaggc tatggtgatt agacctaagt taaacctcac ggagagggtg    60
tgagccatgc actcagttaa gaaggttata ggtagtattg aatttggaat actttcccct    120
caagaaatta ggaa                                                      134
```

<210> SEQ ID NO 138
<211> LENGTH: 224
<212> TYPE: DNA
<213> ORGANISM: Aeropyrum pernix

<400> SEQUENCE: 138

```
ctgctgcagg agataaccag tatgatgata aagccggaac tcaaggtagc cgacaagata    60
tccgtcatca gaaagtcgt cggcgactat acatgattac cccatttaa ttctcggatt     120 tcggggtgt tgggtgctat gtctctaagg ctctcggagt tccgcgagac aaaccttcta    180
gataagatac tctttggcgt cttaagcccc catgagataa ggca                    224
```

<210> SEQ ID NO 139
<211> LENGTH: 26
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (6)..(7)
<223> OTHER INFORMATION: n = a, g, c or t/u
<220> FEATURE:
<221> NAME/KEY: misc_feature
<222> LOCATION: (9)
<223> OTHER INFORMATION: n = a, g, c or t/u
<220> FEATURE:
<221> NAME/KEY: misc_feature
<222> LOCATION: (12)
<223> OTHER INFORMATION: n = a, g, c or t/u
<220> FEATURE:
<221> NAME/KEY: misc_feature
<222> LOCATION: (18)
<223> OTHER INFORMATION: n = a, g, c or t/u
<220> FEATURE:
<221> NAME/KEY: misc_feature
<222> LOCATION: (21)
<223> OTHER INFORMATION: n = a, g, c or t/u
<220> FEATURE:
<221> NAME/KEY: misc_feature
<222> LOCATION: (24)
<223> OTHER INFORMATION: n = a, g, c or t/u

<400> SEQUENCE: 139

```
marccnntng gngaymgngt natngt                                         26
```

<210> SEQ ID NO 140
<211> LENGTH: 186
<212> TYPE: DNA
<213> ORGANISM: Pasteurella multocida

<400> SEQUENCE: 140

```
gaaaaaattg atggcgaaga agtgttaatt atttctgaaa acgatatttt agccattgtt    60
gaataatttt tatcaacaac acaaaatcgt tatttctata aataaacaaa cttaaaatag   120
caatttgcat aacaagattc gaaatgagag gaagataaaa aatggcagca aaagacgtaa   180
aatttg                                                             186
```

<210> SEQ ID NO 141
<211> LENGTH: 113
<212> TYPE: DNA
<213> ORGANISM: Haemophilus influenzae

<400> SEQUENCE: 141

```
gaaaaaatcg atggtgaaga agtgttaatc atttctgaaa acgacatcct agcaattgta    60
gaataattat taaataaggg aaaagaaaat ggcagcaaaa gacgtaaaat ttg          113
```

<210> SEQ ID NO 142
<211> LENGTH: 113
<212> TYPE: DNA
<213> ORGANISM: Haemophilus ducreyi

<400> SEQUENCE: 142

```
gaaaaaattg atggcgaaga aattttaatt ctttcagaga atgacattct tgcaattgta    60
gaataatcga agaataaggg ataataaaat ggcaataaaa gacgttaaat ttg          113
```

<210> SEQ ID NO 143
<211> LENGTH: 137
<212> TYPE: DNA
<213> ORGANISM: Buchnera aphidicola

<400> SEQUENCE: 143

```
gaaaaaattg ataacgaaga attattaatt ctaactgaaa gcgacatttt agcaattgtt    60
gaatagtaaa ccacatgcta tatcattgaa aattgattta aggggatgtc aaatggccgc   120
taaagatgta aaatttg                                                 137
```

<210> SEQ ID NO 144
<211> LENGTH: 139
<212> TYPE: DNA
<213> ORGANISM: Myzus persica

<400> SEQUENCE: 144

```
gaaaaaatta atactgaaga gttattactt ttaactgaaa gtgacatttt agcaattgtt    60
gaatagtaaa ctatatgcta tatccattta aaaatttatt taagggaatg tcaaatggcc   120
gctaaagatg taaaatttg                                               139
```

<210> SEQ ID NO 145
<211> LENGTH: 144
<212> TYPE: DNA
<213> ORGANISM: Vibrio cholerae

<400> SEQUENCE: 145

```
gaaaagatcg atggcaaaga agtgctgatc ttggctgaac atgacatttt ggcaatcgtt    60
gaataattga ttctgaatcc caacgaaatc aataactgaa tttagaaagg aaatgaaaaa   120
tggctgctaa agacgtacgt tttg                                         144
```

<210> SEQ ID NO 146
<211> LENGTH: 137
<212> TYPE: DNA
<213> ORGANISM: Escherichia coli

<400> SEQUENCE: 146

| gagaagatcg acaatgaaga agtgttgatc atgtccgaaa gcgacattct ggcaattgtt | 60 |
| gaagcgtaat cctcgcacga cactgaacat acgaatttaa ggaataaaga taatggcagc | 120 |
| taaagacgta aaattcg | 137 |

<210> SEQ ID NO 147
<211> LENGTH: 137
<212> TYPE: DNA
<213> ORGANISM: Escherichia coli

<400> SEQUENCE: 147

| gagaagatcg acaatgaaga agtgttgatc atgtccgaaa gcgacattct ggcaattgtt | 60 |
| gaagcgtaat cctcgcacga cactgaacat acgaatttaa ggaataaaga taatggcagc | 120 |
| taaagacgta aaattcg | 137 |

<210> SEQ ID NO 148
<211> LENGTH: 137
<212> TYPE: DNA
<213> ORGANISM: Escherichia coli

<400> SEQUENCE: 148

| gagaagatcg acaatgaaga agtgttgatc atgtccgaaa gcgacattct ggcaattgtt | 60 |
| gaagcgtaat ccgcgcacga cactgaacat acgaatttaa ggaataaaga taatggcagc | 120 |
| taaagacgta aaattcg | 137 |

<210> SEQ ID NO 149
<211> LENGTH: 142
<212> TYPE: DNA
<213> ORGANISM: Pseudomonas putida

<400> SEQUENCE: 149

| gtgaaagtcg atggcgaaga cctgctggta atggccgaga acgagattct cgccgttatc | 60 |
| gaaggctgat ttccccgact tcccgttatt ccaaagcatt tcaaggatta aacgatcatg | 120 |
| gctgctaaag acgtaaaatt cg | 142 |

<210> SEQ ID NO 150
<211> LENGTH: 144
<212> TYPE: DNA
<213> ORGANISM: Pseudomonas aeruginosa

<400> SEQUENCE: 150

| atcaaggtcg atggcgagga actgctggtg atgggcgagt ccgaaatcct cgccgtcctg | 60 |
| gaagactgat cggtctcacc actccgtttt caccgaattc gatttagagg aaagagaaca | 120 |
| tggctgccaa agaagttaag ttcg | 144 |

<210> SEQ ID NO 151
<211> LENGTH: 186
<212> TYPE: DNA
<213> ORGANISM: Neisseria meningitidis

<400> SEQUENCE: 151

| gtaaaagccg acggcgaaga gctgttggta atgcgcgaag aagatatttt cggcatcgtt | 60 |
| gaaaaataaa tacggacacg atgccgtctg aaacggcaaa ccgccttcag acggcataaa | 120 |
| cggtttttatc agacagtttt aatgattttt ggagaattga aatggcagca aaagacgtac | 180 |

```
aattcg                                                                   186

<210> SEQ ID NO 152
<211> LENGTH: 186
<212> TYPE: DNA
<213> ORGANISM: Neisseria meningitidis

<400> SEQUENCE: 152
gtaaaagccg acggcgaaga gctgttggta atgcgcgaag aagatatttt cggcatcgtt        60
gaaaaataaa tacggacacg atgccgtctg aaacggcaaa ccgccttcag acggcataaa       120
cggttttatc agacagtttt aatgattttt ggagaattga atggcagca aaagacgtac        180 agttcg                                                                  186

<210> SEQ ID NO 153
<211> LENGTH: 185
<212> TYPE: DNA
<213> ORGANISM: Neisseria gonorrhoeae

<400> SEQUENCE: 153
gtaaaagccg acggcgaaga gctgttggta atgcgcgaag aagatatttt cggcatcgtt        60
gaaaaataaa tacggacacg atgccgtctg aaacggcaaa ccgccttcag acggcataaa       120
cggttttatc agacagtttt aagattttg gagaattgaa atggcagcaa aagacgtaca       180
attcg                                                                   185

<210> SEQ ID NO 154
<211> LENGTH: 201
<212> TYPE: DNA
<213> ORGANISM: Xylella fastidiosa

<400> SEQUENCE: 154
tacaaggctg aaggcgtcga atacaaagta ttacgcgagg acgacatcct ggcgatcatc        60
ggttgattaa gccaagcccg aaactcgtga atgcatccga catatcacgc aacagcggg       120 cacattgttc catacatcac taatgttctc atcgcgaatc ttggagtaaa acataatgg       180 ctgccaaaga aattattttc a                                                 201

<210> SEQ ID NO 155
<211> LENGTH: 224
<212> TYPE: DNA
<213> ORGANISM: Streptomyces coelicolor

<400> SEQUENCE: 155
gtgaagtaca acggcgagga gtacctcgtc ctctcggccc gcgacgtgct cgcgatcgtc        60
gagaagtaga agtagtactt cgcttcaccg aagcaccttg ctttccagct gcgcccctgg       120
ctcccgcgac cataaaaagc cgggcgtcgg gggcgcagtt gccgtataac cccaagattt       180
ccggaagagg gctcacgctc ccatggcgaa gatcctgaag ttcg                        224

<210> SEQ ID NO 156
<211> LENGTH: 185
<212> TYPE: DNA
<213> ORGANISM: Mycobacterium tuberculosis

<400> SEQUENCE: 156
atcaagtaca acggcgagga atacctgatc ctgtcggcac gcgacgtgct ggccgtcgtt        60
tccaagtagt agagcgtgtt ccgccccggc gatccccgtg ctcaccacgg gtgatttccg       120
gggcggcatg cgttagcgga ctagccctgc gtagaggagc ctgatgagca agctgatcga       180
```

```
atacg                                                                    185

<210> SEQ ID NO 157
<211> LENGTH: 185
<212> TYPE: DNA
<213> ORGANISM: Mycobacterium tuberculosis

<400> SEQUENCE: 157
atcaagtaca acggcgagga atacctgatc ctgtcggcac gcgacgtgct ggccgtcgtt          60
tccaagtagt agagcgtgtt ccgccccggc gatccccgtg ctcaccacgg gtgatttccg        120
gggcggcatg cgttagcgga ctagccctgc gtagaggagc ctgatgagca agctgatcga        180
atacg                                                                    185

<210> SEQ ID NO 158
<211> LENGTH: 169
<212> TYPE: DNA
<213> ORGANISM: Mycobacterium leprae

<400> SEQUENCE: 158
atcaagtaca atggcgagga atacctgatc ctgtcggcac gtgacgtgct ggctgtcgta         60
tccaagtaac gaaccgtgtt ccgccccggc gatccccgtg cttaaccacg ggtgatttcc        120
ggggcggcat gcgtttaaag gagcctgatg agcaagctga ttgagtacg                    169

<210> SEQ ID NO 159
<211> LENGTH: 103
<212> TYPE: DNA
<213> ORGANISM: Thermus aquaticus

<400> SEQUENCE: 159
attgagattg caccgcgaag gacgtacgtg atcctctccg agcgcgacct gcttgcggtc         60
ctgcagtaaa ggaggtgaac catggcgaag atcctggtgt ttg                         103

<210> SEQ ID NO 160
<211> LENGTH: 100
<212> TYPE: DNA
<213> ORGANISM: Thermus thermophilus

<400> SEQUENCE: 160
attgagattg acggcgagga gtacgtgatc ctctccgagc gcgacctgct tgcggtcctg         60
cagtaaagga ggtgaaccat ggcgaagatc ctggtgtttg                             100

<210> SEQ ID NO 161
<211> LENGTH: 100
<212> TYPE: DNA
<213> ORGANISM: Thermus thermophilus

<400> SEQUENCE: 161
attgagattg acggcgagga gtacgtgatc ctctccgagc gcgacctgct tgcggtcctg         60
cagtaaagga ggtgaactat ggcgaagatc ctggtgtttg                             100

<210> SEQ ID NO 162
<211> LENGTH: 162
<212> TYPE: DNA
<213> ORGANISM: Deinococcus radiodurans

<400> SEQUENCE: 162
gtcagcctcg aaggcaagaa ctacagcctg ctgagcgagc gcgacctgct cgccattgtc         60
```
gagtaaggct ccgagtcagg ttctgagcct gttcgtttcc tgttttcctt cctcatttca    120
cttttcaagg agcaatcaca atggctaaac agctcgtgtt tg                        162

<210> SEQ ID NO 163
<211> LENGTH: 121
<212> TYPE: DNA
<213> ORGANISM: Porphyromonas gingivalis

<400> SEQUENCE: 163
atagagctgg agggcgaaaa atatatcatc atgcgccaaa acgatgtctt ggcaatcatc     60
taattctcag agacaataac ctacaataaa aataaagac tatggcaaaa gaaatcaaat     120
t                                                                    121

<210> SEQ ID NO 164
<211> LENGTH: 134
<212> TYPE: DNA
<213> ORGANISM: Bacillus subtilis

<400> SEQUENCE: 164
gtgaaatacg aaggtactga atacttaatc ttacgtgaaa gcgacatttt agctgttatc     60
ggctaattct taaataaaca atacttaaaa catttgagga ggtcttgtaa acatggcaaa    120
agaaattaag ttta                                                      134

<210> SEQ ID NO 165
<211> LENGTH: 180
<212> TYPE: DNA
<213> ORGANISM: Bacillus halodurans

<400> SEQUENCE: 165
gtaaaatatg atggtaaaga gtatttaatc cttcgtgaaa gcgatattct cgcgattatc     60
ggttaatttt acgtagggtt atccctacat acatgtaaga cgagaggttt ttgtctattc    120
ctcttttgta aaataccatt caggaggttg agaataacat ggcaaaagat attaagttta    180

<210> SEQ ID NO 166
<211> LENGTH: 121
<212> TYPE: DNA
<213> ORGANISM: Lactobacillus zeae

<400> SEQUENCE: 166
gtgaagtatg aaggtcaaga ctaccttgta ttgcatgaaa aagacatcat ggcaattgcg     60
taactaaata atcgatcaat tttgaggtga ataaaaacaa tggcaaaaga aattaaattc    120
t                                                                    121

<210> SEQ ID NO 167
<211> LENGTH: 142
<212> TYPE: DNA
<213> ORGANISM: Clostridium perfringens

<400> SEQUENCE: 167
gttaagttcg agggggaaga atatactatt ttaagacaag acgatatact agcaatagtt 60
gaatagtttt aaaatataag tgatttagat attcataata tatttgggag gtaaattaat 120
atggctaaaa cattattatt cg 142

<210> SEQ ID NO 168
<211> LENGTH: 120
<212> TYPE: DNA
<213> ORGANISM: Clostridium difficile -continued

<400> SEQUENCE: 168
gttaagatag aaggacaaga atacacaata ctaagacaga gtgatgtatt agctgttatt    60
gaataaatat agaataaatt tattaggagg ggtttaaaat ggctaaagaa attaaatttt    120

<210> SEQ ID NO 169
<211> LENGTH: 129
<212> TYPE: DNA
<213> ORGANISM: Clostridium acetobutylicum

<400> SEQUENCE: 169
ataaaagttg acaatgaaga attgttaatt ttaagacagg acgatatttt aggaattgta    60
gaagaataag ctatcaattt tgttaataat tcagggaggg attctaaatg gcaaagcaaa    120
tattatacg    129

<210> SEQ ID NO 170
<211> LENGTH: 141
<212> TYPE: DNA
<213> ORGANISM: Lactobacillus helveticus

<400> SEQUENCE: 170
gttgaatacg aaggtgaaaa gtacttagtc cttcatgaaa aagacatttt agcaattgca    60
aaataattga cgcaattatt agaaattaaa atacgagatt aaggaggcat agataatcta    120
tggcaaaaga tattaaattc t    141

<210> SEQ ID NO 171
<211> LENGTH: 118
<212> TYPE: DNA
<213> ORGANISM: Lactobacillus johnsonii

<400> SEQUENCE: 171
ttgaagtacg aaggcgaaaa gtacttagtt cttcgtgaaa gcgacttatt agctgtcgtt    60
aagtaataaa atttgaaata aaaggtggca tataatatgg ctaaagagat taaattttt    118

<210> SEQ ID NO 172
<211> LENGTH: 143
<212> TYPE: DNA
<213> ORGANISM: Staphylococcus epidermis

<400> SEQUENCE: 172
gtaaaacgtg gcgcccaaac atatttaatt ttaaatgaag aagatatatt agctattata    60
gaataaagag cgaattttaa atattaatta aatgatttaa taagtggagg ttgtttagac    120
tatggcaaaa gatcttaaat tct    143

<210> SEQ ID NO 173
<211> LENGTH: 163
<212> TYPE: DNA
<213> ORGANISM: Staphylococcus aureus

<400> SEQUENCE: 173
gttaaacgag ataatgaaac atatctagta ttaaatgaag aagatatttt agcggtaatt    60
gaataatata aaattaaatt catagataaa ttgtaaagaa cgaaaatgaa atatgactaa    120
acaaatggag gttatcatt tatggttaaa caattgaaat tct    163

<210> SEQ ID NO 174
<211> LENGTH: 106
<212> TYPE: DNA

<213> ORGANISM: Streptococcus pneumoniae

<400> SEQUENCE: 174

```
gtcaaagatg gcgatgaaaa gtacatcatc gtaggcgaag ctaacatttt ggcaatcatt      60
gaggaataga aggagaaagt aagtatgtca aaagaaatta aatttt                    106
```

<210> SEQ ID NO 175
<211> LENGTH: 175
<212> TYPE: DNA
<213> ORGANISM: Lactococcus lactis

<400> SEQUENCE: 175

```
gtaaaaatgg atggtgaaga attcttgatt ctcaaagatt cagaccttct tgcaattgta      60
gagtaaaatt ataaaagcaa tcattttttt ggttgtcttt tgtctatctt aaaatctata    120
aaattaaaaa tatattctta aaaaggagct aaaatgtcaa agatattaa attttt          175
```

<210> SEQ ID NO 176
<211> LENGTH: 111
<212> TYPE: DNA
<213> ORGANISM: Rickettsia prowasekii

<400> SEQUENCE: 176

```
attgaaataa aaggagaaaa attaatcgtt atgaaagaaa gcgatgtatt tggtattatt      60
aattaattat ttttaggaga aaaaatatga caacgaaact tattaaacac g              111
```

<210> SEQ ID NO 177
<211> LENGTH: 129
<212> TYPE: DNA
<213> ORGANISM: Chlamydia muridarum

<400> SEQUENCE: 177

```
ctcactgtcg aaggtgaaga atatgtcatc gttcaaatga gcgaagttat agcagtcctg      60
caataaaaac taagagagtg aagtaagatt taaggagcgc atcgatggtc gctaaaaata    120
ttaaatata                                                             129
```

<210> SEQ ID NO 178
<211> LENGTH: 128
<212> TYPE: DNA
<213> ORGANISM: Chlamydia trachomatis

<400> SEQUENCE: 178

```
cttactgtcg aaggtgaaga gtacgtcatc gttcaaatga gcgaagttat cgcagttctg      60
caataaaaac taagagagtg aagaagattt aaggagcgca tcaatggtcg ctaaaaacat    120
taaataca                                                              128
```

<210> SEQ ID NO 179
<211> LENGTH: 132
<212> TYPE: DNA
<213> ORGANISM: Chlamydophila pneumoniae

<400> SEQUENCE: 179

```
atcacaatcg atgacgaaga gtatgtcatt ctacagtcca gtgaaatcat ggccgtccta      60
aaataaaata ctagtttgca gattatagaa agttaaggag acaacgatg gcagcgaaaa    120
atattaaata ta                                                         132
```

<210> SEQ ID NO 180
<211> LENGTH: 132

<212> TYPE: DNA
<213> ORGANISM: Chlamydophila pneumoniae

<400> SEQUENCE: 180
atcacaatcg atgacgaaga gtatgtcatt ctacagtcca gtgaaatcat ggccgtccta            60
aaataaaata ctagtttgca gattatagaa agttaaggag aacaacgatg gcagcgaaaa          120
atattaaata ta                                                              132

<210> SEQ ID NO 181
<211> LENGTH: 132
<212> TYPE: DNA
<213> ORGANISM: Chlamydophila pneumoniae

<400> SEQUENCE: 181
atcacaatcg atgacgaaga gtatgtcatt ctacagtcca gtgaaatcat ggccgtccta            60
aaataaaata ctagtttgca gattatagaa agttaaggag aacaacgatg gcagcgaaaa          120
atattaaata ta                                                              132

<210> SEQ ID NO 182
<211> LENGTH: 141
<212> TYPE: DNA
<213> ORGANISM: Chlamydophila caviae

<400> SEQUENCE: 182
cttaccgttg atggtgagga gtacgtcatt gttcaggaaa gcgaagttat ggcagttctc            60
aagtaagaga aatcattatt tatagattgc aaaaagttaa ggagcacaaa aaaacaatgg          120
cagcaaaaaa tattaaatat a                                                    141

<210> SEQ ID NO 183
<211> LENGTH: 160
<212> TYPE: DNA
<213> ORGANISM: Helicobacter pylori

<400> SEQUENCE: 183
ctagaagaca ttctaggcat tgtgggctca ggctcttgtt gtcatacagg taatcatgac            60
cataaacatg ctaaagagca tgaagcttgc tgtcatgatc acaaaaaaca ctaaaaacat          120
tattattaag gatacaaaat ggcaaaagaa atcaaatttt                                160

<210> SEQ ID NO 184
<211> LENGTH: 160
<212> TYPE: DNA
<213> ORGANISM: Helicobacter pylori

<400> SEQUENCE: 184
ctagaagaca ttctaggtat tgtgggctca ggctcttgct gtcatacagg taatcatgac            60
cataaacatg ctaaagagca tgaagcttgc tgtcatgatc acaaaaaaca ctaaaaacat          120
tattattaag gatacaaaat ggcaaaagaa atcaaatttt                                160

<210> SEQ ID NO 185
<211> LENGTH: 72
<212> TYPE: DNA
<213> ORGANISM: Campylobacter jejuni

<400> SEQUENCE: 185
ttagatgata tcttaggaat tttaaaataa tttataaaaa aggataaaaa atggcaaaag            60
aaattatttt tt                                                               72

```
<210> SEQ ID NO 186
<211> LENGTH: 136
<212> TYPE: DNA
<213> ORGANISM: Clostridium thermocellum

<400> SEQUENCE: 186
gtaaaatttg acggacagga atatacgatc ttaagacaaa acgatatttt ggcggtagta      60
gagtaattat attaccaact tcaatacaaa aagtatccta aggaggttaa tcatatggca     120
aagcaaataa aatttg                                                     136

<210> SEQ ID NO 187
<211> LENGTH: 127
<212> TYPE: DNA
<213> ORGANISM: Mycoplasma genitalium

<400> SEQUENCE: 187
tttgagaatg agggaaacaa gtacaaaatt attggatttg aggatgtact tgcctttgaa      60
aaaccagaaa gtggtaagca aagaaaaaga taaaattaaa caattatggc aaaggaatta    120
atctttg                                                              127

<210> SEQ ID NO 188
<211> LENGTH: 138
<212> TYPE: DNA
<213> ORGANISM: Mycoplasma pneumoniae

<400> SEQUENCE: 188
tttgaagagg aaggtaccaa gtacaagatt atttccttgg aagatgtcct tgcttttgaa      60
aagcatggta atacaaaaac tactactgta aagaaaggag ctaagaaaaa atagttatgg    120
caaaggaatt agtatttg                                                  138

<210> SEQ ID NO 189
<211> LENGTH: 120
<212> TYPE: DNA
<213> ORGANISM: Aquifex aeolicus

<400> SEQUENCE: 189
gtagagattg aaggaaagat ttacctcgtt atgtctgaag acgaagtttt agctgttgtt      60
gaagattatt caagcttaat aggaggtgag gtgagatggc agcaaaggca attatctaca    120
```

METHOD FOR DETECTING MICROORGANISMS

The present invention relates to a method for detecting the elements constituting microorganism flora, at least some of the elements of which have an operon in common, characterized in that the elements of said flora are identified by studying the intergenic sequence of said operon.

The human digestive system harbors a considerable number of microorganisms which constitute a microbial flora of extreme complexity. Although these bacteria are distributed throughout the digestive tract, the colon contains most of the flora, both from a quantitative and a qualitative point of view. It is estimated that the colonic flora of an individual consists of $10^{13}$ to $10^{15}$ bacteria, mostly anaerobic bacteria, represented by at least 400 species belonging to approximately 30 different genera. These bacteria colonize the various stages of the colon in a relatively heterogeneous manner. A "fermentation flora" in the cecum and also a "putrefaction flora" in the left colon are conventionally described. Moreover, a residence flora is distinguished from a passing flora. This residence flora is itself divided up into dominant flora and subdominant flora. The dominant bacteria, essentially anaerobic bacteria, are mainly represented by the *Bacteroides* genus, gram-negative bacilli, but also by the *Bifidobacterium, Lactobacillus* or *Clostridium* genera, gram-positive bacilli. The subdominant flora contain aero-anaerobic and microaerophilic bacteria. The presence of enterobacteria and of streptococci is especially noted. Diet, infections, intake of pre- and probiotics and also treatments with antibiotics are all liable to cause drastic modifications in the composition of the colonic flora. Since these variations have a direct impact on health, it is important to be aware of them and to understand them, both in order to avoid them and in order to trigger them for therapeutic purposes. To date, the study of colonic bacteria has made it possible to characterize approximately 200 species. However, this type of investigation comes up against many problems essentially associated with the laboriousness of the techniques. The results obtained and also the conclusions which ensue therefrom are still sketchy.

Bacterial identification is carried out according to various methods which employ either the demonstration of specific phenotypical or biochemical characteristics, or the use and recognition of specific heterologous regions present on the genome.

The beginnings of an identification may be carried out by describing the morphology of the organism studied and by searching, for example, for the presence of endospores, of sheaths, of cysts, of buds, of fruiting bodies, etc. The form of the colonies, the pigmentation, and the origin of the sample are also useful pieces of information. Preliminary studies may also be carried out using dyes specific for the capsule, the flagella, the granules, the wall, etc. However, a more thorough and precise identification necessarily involves techniques comprising isolation on selected media. Such media are developed or improved in order to increase the specificity of the selection. However, it is difficult to completely exclude the presence of possible contaminants which may then interfere in the recognition tests subsequently employed.

These tests make use of the biochemical characteristics specific for a species. Multitest systems exist. They are identification galleries which are provided in the form of kits, of microplates and of strips, the use of which is sometimes automated. However, there exists a certain degree of heterogeneity of chromosomal or plasmid origin within many species. Thus, one or more characteristics will be absent in the identification. Thus, most of the time, only the probability of belonging to a species will be given. A similarity of 80% or more with a reference bacterium will be considered as acceptable. Single-test systems have also been developed. They use synthetic fluorescent substrates for revealing the presence of an enzyme specific for a microorganism. They enable a rapid analysis, but are limited in their use. Specifically, a specific test must be developed for each species.

Immunoassays using poly- or monoclonal antibodies have also been developed. Besides the obvious limitation inherent in polyclonal antibodies, these assays are mainly used to characterize serotypes, but are rarely used to identify species. Although commonly used in hospital diagnosis, they remain relatively unused in bacteriology. As regards the production of monoclonal antibodies, it remains long, laborious and expensive work. They are, for example, directed against lipopolysaccharides, the membrane, the pili, etc., but are, however, rarely specific for a species.

The development of molecular biology techniques has made it possible to develop novel identification assays. These techniques are based on hybridization reactions or polymerase chain amplification reactions (PCR).

Genome/genome hybridization should be greater than or equal to 70% to identify an unknown bacterial species as being the known reference bacterium whose genomic DNA is used to perform the diagnosis. Other assays involve heterologous regions on the DNA specific for a species. The hybridization technique can thus be used, which consists in depositing the product to be analyzed on a nylon or nitrocellulose membrane and then in incubating with a specific labeled probe (cold probe or hot probe) {1}.

It is also possible to use specific primers making it possible to amplify a fragment of a given size by the PCR technique {2, 3}. In this case, the amplificates obtained by PCR can themselves be analyzed by other techniques, such as RFLP (restriction fragment length polymorphism) {4} or TGGE (temperature gradient gel electrophoresis) {5}, refining the diagnosis.

Despite their large capacity for discrimination, these techniques remain limited since they make it possible to analyze only one species at a time, or else consist in isolating a mixture of species which cannot then be identified without knowing exactly the pattern of analysis of the amplificates by a given technique on a given biotope.

The development of DNA chips (biochips) makes it possible to envision a rapid diagnosis relating to several hundreds of species. This technique consists in placing on a surface area of a few millimeters squared several hundreds of DNA sequences specific for a given organism. These probes are hybridized with DNA fragments, generally obtained by RT-PCR. The possible hybridization of said fragments is then observed, and indicates the presence or absence of the gene expressed, or of the organism studied.

The nucleic acid targets studied over the last few years are essentially 16S ribosomal RNA (with more than 7000 available sequences) {1, 2, 4, 5}, the region separating the 16S and 23S genetic loci {3} and the elongation factors {6, 7}. Thus, using 16S RNAs as a basis, it has been possible to detect several new species, belonging to the *Bacteroides* and *Clostridium* groups, but not to the *Bifidobacterium* group {8}. Moreover, and although 16S RNAs make it possible to detect and to identify many bacteria down to the species, they are incapable of discriminating between the various species of staphylococci {2, 3}. Thus, a variable region of the gene encoding HSP 60 has been proposed for studying the microorganisms of the intestinal flora {9}.

A subject of the present invention is a method for detecting and identifying the elements constituting a microorganism flora, in particular the intestinal flora, according to which a target which is even more discriminatory and universal than those already studied is detected and studied.

The method according to the present invention comprises characterizing the sequences of this target for the organisms present in the microbial flora studied, and thus makes it possible to design a diagnostic test.

Thus, the target studied in the method of the invention exhibits strong interspecies heterogeneity, which allows discrimination between the microorganisms.

The present invention therefore relates to a method for detecting the elements constituting a microorganism flora, at least some of the elements of which have an operon in common, characterized in that:

a) the genomic DNA of said flora or the mRNAs is (are) prepared, b) at least some of the noncoding intergenic sequences located in the operon conserved in at least some of the elements of the flora are amplified, and c) the various intergenic sequences amplified are identified in order to determine the elements of said flora.

Specifically, surprisingly, it has been noted that the intergenic regions, in the operons conserved between various species, exhibit a certain heterogeneity, whereas the coding regions which flank said regions in the 5' and/or in the 3' position are generally very conserved. It is possible that this fact is due to a relatively weak selection pressure on the noncoding regions in the course of evolution {10}.

The amplification is preferably carried out by polymerase chain reaction (PCR), but other methods (PCR-like) may be employed, using a pair of primers having nucleotide sequences for implementing the method according to the invention.

The term "PCR-like" is intended to denote all methods using direct or indirect reproductions of nucleic acid sequences, or else in which the labeling systems have been amplified; these techniques are, of course, known. In general, it involves amplification of the DNA with a polymerase; when the sample of origin is an RNA, a reverse transcription should be carried out beforehand. A very large number of methods currently exist for this amplification, such as, for example, the SDA (Strand Displacement Amplification) technique, the TAS (Transcription-based Amplification System) technique, the 3SR (Self-Sustained Sequence Replication) technique, the NASBA (Nucleic Acid Sequence Based Amplification) technique, the TMA (Transcription Mediated Amplification) technique, the LCR (Ligase Chain Reaction) technique, the RCR (Repair Chain Reaction) technique, the CPR (Cycling Probe Reaction) technique, or the Q-beta-replicase amplification technique. Some of these techniques have since been improved.

The analysis of the amplified sequences is advantageously carried out on a DNA kit comprising sequences complementary to the sequences liable to be amplified from the elements of said flora. Knowledge of the microorganisms which may be present in the biological sample studied is therefore important in order to choose the DNA chip to be analyzed. Thus, it is necessary for the DNA chip to have, at its surface, probes specific for each of the organisms intended to be studied. Such a DNA chip is also a subject of the invention.

Thus, the present invention relates most particularly to a DNA chip comprising, at its surface, a plurality of oligonucleotides complementary to the intergenic sequences of the various operons conserved between the species. The term "DNA chip" is intended to mean a solid support to which are attached nucleic acid fragments under conditions which allow hybridization thereof with the complementary oligonucleotides, and detection of the hybrids thus formed. Thus, a DNA chip according to the invention also relates to the membranes as used to perform Southern blotting.

The oligonucleotides attached to the DNA chip according to the present invention are so attached by any conventional method known to those skilled in the art, and are approximately 50 bases long. It is understood that the oligonucleotides considered may also be shorter or longer. Thus, it is within the scope of those skilled in the art to determine the length of the oligonucleotides attached to the chip according to the invention, for each sequence.

Preferably, the oligonucleotides attached to the DNA chip are chosen such that their sequence comprises a part of the hypervariable region identified according to the present invention. The oligonucleotides attached to the chip according to the invention may also contain sequences corresponding to the sequences variable to a lesser degree, located at or close to the end of the operon genes.

In a particular and preferred implementation of the invention, the DNA chip according to the invention has a plurality (a number greater than or equal to 2, preferably 3, more preferably 5, most preferably 10) of oligonucleotides greater than 40 bases long. Preferably, said oligonucleotides comprise a fragment of at least 20, preferably 40 or 50, more preferably 75, most preferably 100 consecutive bases, of the sequences SEQ ID NO: 63 to SEQ ID NO: 138 and SEQ ID NO: 140 to SEQ ID NO: 189, corresponding to the intergenic sequences of various species (rpoBC for SEQ ID NO: 63 to SEQ ID NO: 138, GroESL for SEQ ID NO: 140 to SEQ ID NO: 189).

Thus, demonstrating the possible hybridizations of the amplified sequences makes it possible to identify the elements present in the microbial flora studied.

An operon which is particularly suitable for implementing the method according to the invention is the bacterial rpoBC operon. This bacterial operon contains coding sequences which are relatively homologous between genera. It is therefore possible to determine degenerate primers for amplifying a region which is heterologous between species and which corresponds to the transcribed intergenic region (IGR). In bacteria, the rpoBC operon encodes the beta and beta prime subunits of DNA-directed RNA polymerase, just like the homologous genes, which may or may not be conserved in the form of an operon, in mitochondria and other eukaryotic organelles (chloroplasts), and just like nuclear eukaryotic RNA polymerase II (which synthesizes the messenger RNAs). The study of this operon makes it possible not only to detect the bacteria, but also other eukaryotic microorganisms (yeast, protozoa, or others).

The method according to the invention is thus carried out using degenerate primers located in the coding sequences of the operons, in particular at least one primer chosen from the sequences SEQ ID NO: 1 to SEQ ID NO: 31, themselves a subject of the invention. The RNA polymerase proteins are in fact extremely conserved according to the species, which makes it possible to find amino acid sequences which align with one another, and thus to choose degenerate oligonucleotides for amplifying the intergenic sequences.

The pairs of primers described by the sequences: (a sequence chosen from the sequences SEQ ID NO: 1 to SEQ ID NO: 8)/(a sequence chosen from the sequences SEQ ID NO: 9 to SEQ ID NO: 11) are used to perform a first amplification of the intergenic, IGR, of the bacteria. A second, more specific, amplification can then be carried out using pairs of primers which hybridize within the first amplified region, and which are described by the sequences: (a sequence chosen from the sequences SEQ ID NO: 12 to SEQ ID NO: 15)/(a sequence chosen from the sequence SEQ ID NO: 16 to SEQ ID NO: 31).

```
SEQ ID NO. 1    GGNGAYAARY TNGCNGGNAG NCAYGG
SEQ ID NO. 2    GGNGAYAARY TNGCNGGNCG NCAYGG
SEQ ID NO. 3    GGNGAYAARY TNGCNAAYAG NCAYGG
SEQ ID NO. 4    GGNGAYAARY TNGCNAAYCG NCAYGG
SEQ ID NO. 5    GGNGAYAARA TGGCNGGNMG NCAYGG
SEQ ID NO. 6    GGNGAYAART TYGCNTCNMG NCAYGG
SEQ ID NO. 7    GGNGAYAART TYGCNAGYMG NCAYGG
SEQ ID NO. 8    GGNGAYAART TYGCNACNMG NCAYGG
SEQ ID NO. 9    AAYGCNGAYT TYGAYGGNGA YCARAT
SEQ ID NO. 10   AAYGCNGAYT TYGAYGGNCA RATGGC
SEQ ID NO. 11   AAYGCNGAYT TYGAYGGNGA YGARAT
SEQ ID NO. 12   GGNGGNCARM GNTTYGGNGA RATGGA
SEQ ID NO. 13   GGNGGNCAYG GNTTYGGNGA RATGGA
SEQ ID NO. 14   GGNGGNCARW SNTTYGGNGA RATGGA
SEQ ID NO. 15   GGNGGNNTNM GNTTYGGNGA RATGGA
SEQ ID NO. 16   GGNAARCGNG TNGAYTAYTC NGGNMG
SEQ ID NO. 17   GGNAARCGNG TNGAYTAYAG NGGNMG
SEQ ID NO. 18   GGNAARAGNG TNGAYTAYTC NGGNMG
SEQ ID NO. 19   GGNAARAGNG TNGAYTAYAG NGGNMG
SEQ ID NO. 20   GGNAARCGNG GNGAYTAYTC NGTNMG
SEQ ID NO. 21   GGNAARCGNG GNGAYTAYAG NGTNMG
SEQ ID NO. 22   GGNAARAGNG GNGAYTAYTC NGTNMG
SEQ ID NO. 23   GGNAARAGNG GNGAYTAYAG NGTNMG
SEQ ID NO. 24   GGNAARCGNG TNGAYTTYTC NGGNMG
SEQ ID NO. 25   GGNAARCGNG TNGAYTTYAG NGGNMG
SEQ ID NO. 26   GGNAARAGNG TNGAYTTYTC NGGNMG
SEQ ID NO. 27   GGNAARAGNG TNGAYTTYAG NGGNMG
SEQ ID NO. 28   GGNAARCGNG TNGAYTTYTC NGCNMG
SEQ ID NO. 29   GGNAARCGNG TNGAYTTYAG NGCNMG
SEQ ID NO. 30   GGNAARAGNG TNGAYTTYTC NGCNMG
SEQ ID NO. 31   GGNAARAGNG TNGAYTTYAG NGCNMG
```

The pairs of primers described by the sequences: (a sequence chosen from the sequence SEQ ID NO: 53 to SEQ ID NO: 54 are used to amplify a the intergenic region, IGR, of the bacteria.

```
FO   SEQ ID NO. 53   GGNGGNCANN SNTTYGGNGA RATGGA
RP   SEQ ID NO. 54   AAYGCNGAYT TYGAYGGNGA YSARAT
```

```
                        -continued
FO   SEQ ID NO. 55   GGNGGNCARM GNTTYGGNGA RATGGA
     SEQ ID NO. 56   GGNGGNCAYG GNTTYGGNGA RATGGA
     SEQ ID NO. 57   GGNGGNCARW SNTTYGGNGA RATGGA
     SEQ ID NO. 58   GGNGGNNTNM GNTTYGGNGA RATGGA
     SEQ ID NO. 59   AAYGCNGAYT TYGAYGGNGA YCARAT
     SEQ ID NO. 60   AAYGCNGAYT TYGAYGGNCA RATGGC
     SEQ ID NO. 61   AAYGCNGAYT TYGAYGGNGA YGARAT
```

These primers were designed based on the study of the degeneracy of conserved protein motifs corresponding to rpoB and/or encoded by the rpoB gene:

```
beta 2 I;
coryneb/bif/actinom/camp/pseudom/salmon/esch/
vibrio/clos/bact/hel/citrob/prot/haf/yers/past/
actinob/aer
SEQ ID NO. 55 GGNGGNCARM GNTTYGGNGA RATGGA    (8 deg)
Beta 2 ii:
bacillus
SEQ ID NO. 56 GGNGGNCAYG GNTTYGGNGA RATGGA    (7 deg)
beta 2 iii:
helicobacter mustelae
SEQ ID NO. 57 GGNGGNCARW SNTTYGGNGA RATGGA    (8 deg)
beta 2 iv:
archae (methano)
SEQ ID NO. 58 GGNGGNNTNM GNTTYGGNGA RATGGA    (9 deg)
FO:
2 I/II/III:  GGNGGNCANN SNTTYGGNGA RATGGA
(SEQ ID NO. 53)
```

For the reverse sequences, determined based on the degeneracy of conserved protein motifs corresponding to rpoC and/or encoded by the rpoC gene

```
beta p 2 i:
coryneb/bif/actinom/bac/camp/pseudom/salmon/esch/
vibrio/clos/bact/hel/citrob/prot/haf/yers/past/
actinob/aer/staph/lactob/enteroc/lactoc
SEQ ID NO. 59 AAYGCNGAYT TYGAYGGNGA YCARAT    (8 deg)
beta p 2 ii:
archae (methano)
SEQ ID NO. 61 AAYGCNGAYT TYGAYGGNGA YGARAT    (8 deg)
beta p 2 iii:
streptoc
SEQ ID NO. 60 AAYGCNGAYT TYGAYGGNCA RATGGC    (7 deg)
RP: P 2 i/ii: AAYGCNGAYT TYGAYGGNGA YSARAT
(SEQ ID NO. 54)

<<REVERSE>>   ATYTSRTCNC CRTCRAARTC NGCRTT
(SEQ ID NO. 62)
```

These primers are also part of the invention.

A subject of the invention is also the genomic sequences of microorganisms which may be amplified by the primers according to the invention, in particular the pairs of primers:

(a sequence chosen from the sequences SEQ ID NO: 1 to SEQ ID NO: 8)/(a sequence chosen from sequences SEQ ID NO: 9 to SEQ ID NO: 11), and the pairs of primers: (a sequence chosen from the sequences SEQ ID NO: 12 to SEQ ID NO: 15)/(a sequence chosen from the sequences SEQ ID NO: 16 to SEQ ID NO: 31). Amplification with pairs of primers: (a sequence chosen from the sequences SEQ ID NO: 53, SEQ ID NO: 55 to SEQ ID NO: 58)/(a sequence chosen from the sequences SEQ ID NO: 54, SEQ ID NO: 59 to SEQ ID NO: 61) is also envisioned.

Thus, a subject of the invention is also in particular a sequence from SEQ ID NO: 63 to SEQ ID NO: 138, which correspond to the hypervariable intergenic regions of the rpoB operon or various organisms. A subject of the invention is also a fragment of a minimum of 20 bases, preferably 30 bases, more preferably 50 bases, even more preferably 75 bases, most preferably 100 bases of one of the sequences SEQ ID NO: 63 to SEQ ID NO: 138, or the sequences complementary thereto, it being possible for said fragment to be used to define organism-specific primers, or for the identification of organisms, in particular by hybridization.

Thus, the DNA chip according to the invention preferably has, at its surface, a plurality of oligonucleotides (a minimum of two) comprising fragments chosen from the fragments of the sequences SEQ ID NO: 63 to SEQ ID NO: 138 defined above, thus allowing the identification of microorganisms. The length of these oligonucleotides can be determined by those skilled in the art, as a function of the hybridization conditions which they intend to use. Oligonucleotides approximately 50 bases long are thus envisioned.

Another operon which is particularly suitable for implementing the method according to the invention is the bacterial GroESL operon. This bacterial operon is bicistronic and contains coding sequences which are relatively homologous between genera. It is therefore also possible to determine degenerate primers to amplify a region which is heterologous between species and which corresponds to the transcribed intergenic region (IGR). In bacteria, the GroESL operon encodes the HSP10 and HSP60 proteins (heat shock proteins of 10 and 60 kDa respectively), just like the homologous genes, which may or may not be conserved in the form of an operon, in mitochondria and other eukaryotic organelles (chloroplasts). The study of this operon makes it possible not only to detect bacteria, but also other eukaryotic microorganisms (yeasts, protozoa, or others).

The method according to the invention is thus carried out using degenerate primers located in the coding sequences of the operons. The HSP proteins are in fact extremely conserved according to species, which makes it possible to find amino acid sequences which align with one another, and thus to choose degenerate oligonucleotides to amplify the intergenic, promoter or terminator sequences.

Preferably, the primers described by the sequences SEQ ID NO: 32 and SEQ ID NO: 33 are used to amplify the intergenic region, IGR, of *E. coli* and of Enterobacteriaceae.

```
ENT-BDEG:
CTGGAYGTKA ARRTNGGYGA YATYGT      (SEQ ID NO. 32)

ENT-ADEG:
ANNACNGTNG CRGTRGTGGT RCCGTC      (SEQ ID NO. 33)
```

Other degenerate primers can also be used to implement the protocol according to the invention, in particular any primer chosen from the sequences SEQ ID NO: 34 to SEQ ID NO: 52.

```
UNI-ADEG 1:
GGNGAYGGNA CNACNACNGC NACNNT      (SEQ ID NO. 34)

UNI-ADEG 2:
GGNGAYGGNA CNACNACNTG NTCNNT      (SEQ ID NO. 35)

ENT-BNEW:
AANMTTCGTC CNYTRCANGA YCGNGT      (SEQ ID NO. 36)

CLO-BNEW2:
ATNARRCCAY TWGGWGAYMG NGTWGT      (SEQ ID NO. 37)

BIF-BNEW:
AARCCRCTCG AGGACMRNRT NSTSGT      (SEQ ID NO. 38)

UNI-A3:
GGNGAYGGNA CNAANACNGC NACNNT      (SEQ ID NO. 39)

BIF-BNEW2:
ATCAAGCCNC TMGRRGACMR SRTNST      (SEQ ID NO. 40)

HEL-BNEW:
NTNCANCCNT TNGGNGANAG NGTNTT      (SEQ ID NO. 41)

CAM-BNEW:
NTNCANCCNT TNGGNAANCG NGTNCT      (SEQ ID NO. 42)

BACT-BNEW:
NTNAANCCNT TNGCNGANCG NGTNCT      (SEQ ID NO. 43)

CHLA-BNEW:
NTNAANCCNT TNGGNGANAG NATNTT      (SEQ ID NO. 44)

MYCP-BNEW:
NTNAAACCNNTNGGNAANCGNGTNAT        (SEQ ID NO. 45)

STA-BNEW:
NTNAAACCNNTNGGNAANCGNGTNAT        (SEQ ID NO. 46)

LACC-BNEW:
TTGAAACCNTTAGNGRAYCGYGTRST        (SEQ ID NO. 47)

LACB-BNEW:
TTAMARCCAWTMGGNGATCGNGTNRT        (SEQ ID NO. 48)

CLO-BNEW3:
ATNANACCANTNGGNGACAGNGTNGT        (SEQ ID NO. 49)

ENT-BNEW2:
NTNCGNCCNTTNCANGANCGNGTNAT        (SEQ ID NO. 50)

LEG-BNEW:
NTNCGNCCNTTNCANGANCGNGTNGT        (SEQ ID NO. 51)

AER-BNEW:
NTNCGNCCNCTNCANGANCGNGTNAT        (SEQ ID NO. 52)

LACB-BNEW2:
MARCCNNTNG GNGAYMGNGT NATNGT      (SEQ ID NO. 139)
```

These primers are also subjects of the present invention. Preferably, the detection of a microorganism is carried out using a pair of primers SEQ ID NO: 32/SEQ ID NO: 33, or (SEQ ID NO: 34, SEQ ID NO: 35 or SEQ ID NO: 39)/(a sequence chosen from the sequences SEQ ID NO: 36 to SEQ ID NO: 38 or SEQ ID NO: 40 to SEQ ID NO: 52).

The sequences SEQ ID NO: 36 to SEQ ID NO: 38 and/or SEQ ID NO: 40 to SEQ ID NO: 52 and/or SEQ ID NO: 139, used in particular in amplification reactions with sequences SEQ ID NO: 34, SEQ ID NO: 35 and/or SEQ ID NO: 39, make it possible, respectively, to detect the microorganisms and species listed below. One or more pair(s) of sequences may be used in an amplification reaction.

Thus, the sequences according to the present invention make it possible in particular to detect microorganisms of the following genera and families: *Lactococcus* (SEQ ID NO: 39), *Bifidibacterium* (SEQ ID NO: 38 and/or 40),

*Mycobacterium* (SEQ ID NO: 40), *Helicobacter* (SEQ ID NO: 41), *Campylobacter* (SEQ ID NO: 42), *Bacteroides* (SEQ ID NO: 43), *Chlamydia* (SEQ ID NO: 44), *Mycoplasma* (SEQ ID NO: 45), *Staphylococcus* (SEQ ID NO: 46), *Lactococcus* and/or *Streptococcus* (SEQ ID NO: 47), *Lactobacillus* and/or *Bacillus* (SEQ ID NO: 48), *Clostridium* (SEQ ID NO: 37 and/or 49), Enterobacteriaceae (SEQ ID NO: 36 and/or 50), *Pasteurella* and/or *Haemophilus* (SEQ ID NO: 50), *Neisseria* and/or *Legionella* (SEQ ID NO: 51), *Aeromonas* and/or *Bordetella* (SEQ ID NO: 52), *Lactobacillus* and/or *Bacillus* (SEQ ID NO: 139).

The subject of the invention is also the genomic sequences of microorganisms which can be amplified using the primers according to the invention, in particular the pairs of primers SEQ ID NO: 32/SEQ ID NO: 33, and (SEQ ID NO: 34, SEQ ID NO: 35 or SEQ ID NO: 39)/(a sequence chosen from the sequences SEQ ID NO: 36 to SEQ ID NO: 38, SEQ ID NO: 40 to SEQ ID NO: 52 or SEQ ID NO: 139).

Thus, a subject of the invention is also in particular a sequence from SEQ ID NO: 140 to SEQ ID NO: 189, which correspond to the hypervariable intergenic regions of the GroESL operon of various organisms. A subject of the invention is also any fragment of a minimum of 20 bases, preferably 30 bases, more preferably 50 bases, even more preferably 75 bases, most preferably 100 bases of one of the sequences SEQ ID NO: 140 to SEQ ID NO: 189, or the sequences complementary thereto, it being possible for said fragment to be used to define organism-specific primers, or for the identification of organisms, in particular by hybridization.

Thus, the DNA chip according to the invention preferably has, at its surface, a plurality of oligonucleotides (a minimum of two) comprising fragments chosen from the fragments of the sequences SEQ ID NO: 140 to SEQ ID NO: 189 defined above, thus allowing the identification of the microorganisms. The length of these oligonucleotides can be determined by those skilled in the art, as a function of the hybridization conditions, which they intend to use. Oligonucleotides approximately 50 bases long are thus envisioned.

Subjects of the present invention are also diagnostic kits for carrying out the method according to the invention. These diagnostic kits contain degenerate primers for amplifying one or more intergenic regions of operon which is conserved among species. They may also contain the reagents required for the amplification reaction. Moreover, DNA representing positive or negative controls may be included in the diagnostic kits according to the invention.

A diagnostic kit according to the invention also advantageously contains the elements required for analyzing the amplified products. In particular, a diagnostic kit according to the invention contains a DNA chip according to the invention, which has, at its surface, the sequences corresponding to the various microorganisms.

Depending on the species it is desired to detect, the diagnostic kit according to the invention contains the appropriate pair of primers and analytical elements. Furthermore, a kit according to the invention may also comprise instructions for carrying out the method according to the invention.

A diagnostic kit according to the invention may also only contain a DNA chip according to the invention, and optionally also instructions for carrying out the analysis of fragments located in the intergenic region of operons which are conserved between species, the preferred operons being GroESL and rpoBC.

The coupling of specific primers and probes thus allows rapid and precise identification of the flora of a given individual. It is therefore possible to establish the profile(s) of populations characteristic of healthy individuals. It is also possible to establish the standard profiles for various pathological conditions.

The method according to the invention also provides the possibility of easy monitoring of the evolution of the flora as a function of diet. More specifically, it is possible to follow the effects, in the colon, of a particular food, such as a pre- or probiotic, or of a medicinal treatment such as a treatment with antibiotics.

It is therefore possible to envision the development of foods or medicinal products for "effect on the flora" purposes, allowing reestablishment and a return to a normal profile after an imbalance subsequent to any pathological condition or attack. It is also possible to use primers and probes corresponding to pathogenic strains in order to optionally establish critical population thresholds preceding a pathological condition. It is then possible to determine which of the other populations are liable to exert a barrier effect on these pathogens.

The tools for diagnosing the intestinal flora developed and based on the method according to the invention (which are also subjects of the invention) are of interest firstly to industrial companies in the agrofoods and pharmacy domains, in order to develop their products and to determine the impact thereof on the intestinal flora. Specifically, particular diets are liable, in the long term, to significantly modify the composition of the flora and, consequently, to have harmful or beneficial effects depending on the types of population which appear or disappear. Similarly, medicinal treatments, and in particular antibiotic treatments, lead to imbalances in the microflora. Characterization of the populations affected according to the type of medicinal product would make it possible to set up a parallel or subsequent treatment capable of preventing these modifications or of reestablishing a correct flora as rapidly as possible.

These tools are also of interest to health professionals, for characterizing the intestinal flora of patients, which may make it possible, for example, to direct a treatment. Specifically, gastroenterologists estimate that 70% of the population of industrialized countries complain of diverse digestive disorders, which are called functional colopathy, ranging from simple digestive disorders such as bloating or flatulence, to more significant disorders such as constipation or diarrhea, etc. The majority of their consultations concern this functional colopathy.

Few solutions are provided to treat these disorders since, for certain types of colopathy, their cause is still quite unknown, and for others, there is no effective treatment. Added to this is the problem of the medical diagnosis since the patients presenting these symptoms of functional colopathy do not generally present any physical lesion in the colon. Only a questionnaire enables the gastroenterologist to turn toward a type of treatment, which proves to be relatively ineffective in the majority of cases. The market for products which can relieve these disorders is therefore considerable, as is that for diagnosis. Specifically, a diagnosis of the state of the flora of the patients might provide the physician with information regarding the causes of their disorders and the treatment to be carried out.

In order to select a genomic target of interest, namely a target which is conserved in all the genomes, the conservation of the most conserved operons in the course of evolution was studied based on the genomes of the 51 bacteria entirely sequenced and available on the NCBI server. These sequences were positioned relative to that of rpoB/C (beta operon).

It emerged from this first analysis that the longest and most conserved targets are in fact the GroESL operons (encoding Hsp10 (groES) and Hsp60 (groEL)) and a part of the beta operon corresponding to the rpoB and rpoC genes (encoding the beta and beta' subunits of DNA-directed RNA polymerase). In addition, it was possible to identify conserved protein motifs sufficiently long to allow the definition and then the synthesis of universal (ubiquitous), or almost universal, degenerate primers.

Thus, these two operons were chosen in order to exemplify the principle of the method according to the invention.

Finally, the region of interest of the beta operon was amplified, i.e. the region amplifiable by PCR, using the two corresponding degenerate primers (FO and RP: SEQ ID NO: 53 and SEQ ID NO: 54) for selection of bacteria in order to establish the sequence thereof and to test them by hybridization on a nylon membrane so as to validate this specificity. These sequences were also aligned to their homologs available on GenBank in order to observe this specificity by bioinformatics.

The same experiments were carried with the GroESL operon, and it can thus be shown that the method according to the invention makes it possible to identify and discriminate between the various species of microorganisms.

The following examples are intended to illustrate the invention, and should not be considered as limiting the invention.

In the application, the abbreviations for the bacteria are as follows:

*Bacillus subtilis* (BS) CIP 52-65T; *Bacteroides vulgatus* (BV) DSM 1447; *Bifidobacterium longum* (BL) DSM 20219; *Clostridium leptum* (CL) DSM 753; *Clostridium nexile* (CN) DSM 1787; *Clostridium spiroforme* (CS) DSM 1552; *Clostridium glycolycum* (CG) DSM 1288; *Lactobacillus gaseri* (LG) DSM 20077; *Lactobacillus helveticus* (LH) CIP 103146; *Lactobacillus paracasei* (LP) DSM 8741; *Lactobacillus reuteri* (LR) DSM 20053; *Pseudomonas aeruginosa* (PA) CIP100720; *Ruminococcus hydrogenotrophicus* (RH) DSM 10507; *Citrobacter freundii* (CF); *Serratia liquefaciens* (SL); *Serratia marcescens* (SM); *Enterobacter cloacae* (EnC); *Escherichia coli* (EsC); *Morganella morganii* (MM); *Proteus mirabilis* (PM); *Klebsiella oxytoca* (KO); *Klebsiella pneumoniae* (KP).

EXAMPLES

Example 1

Isolation of Strains

Figure 1:
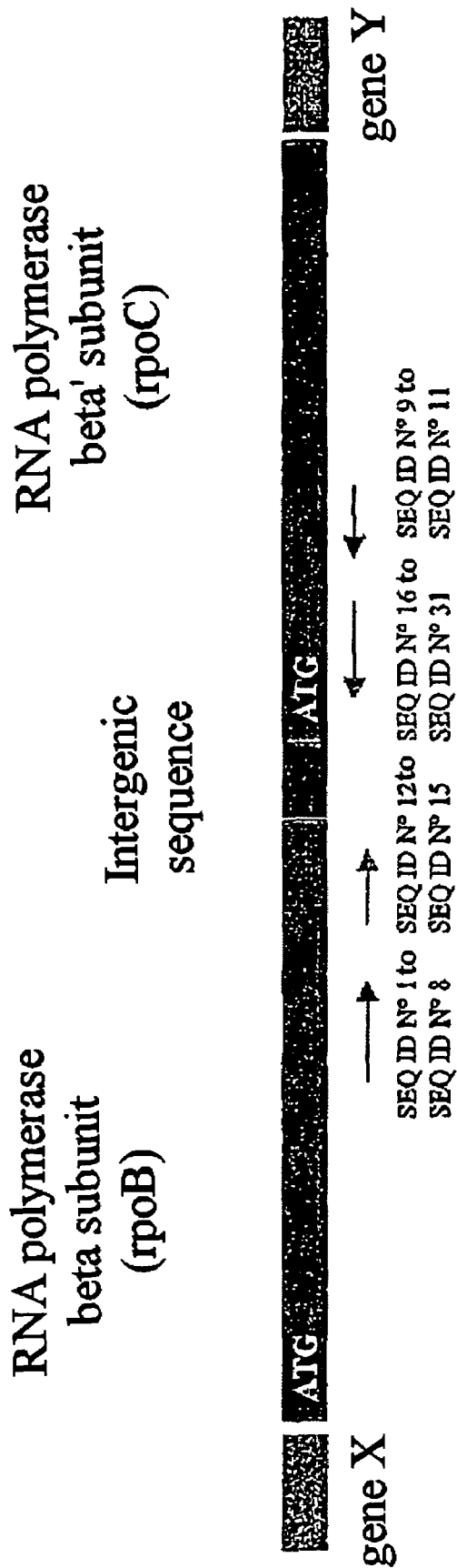
FIG. 1: Diagram of the rpoBC operon of *E. coli*. The universal (ubiquitous) primers are used to amplify the intergenic sequence.
Figure 2:
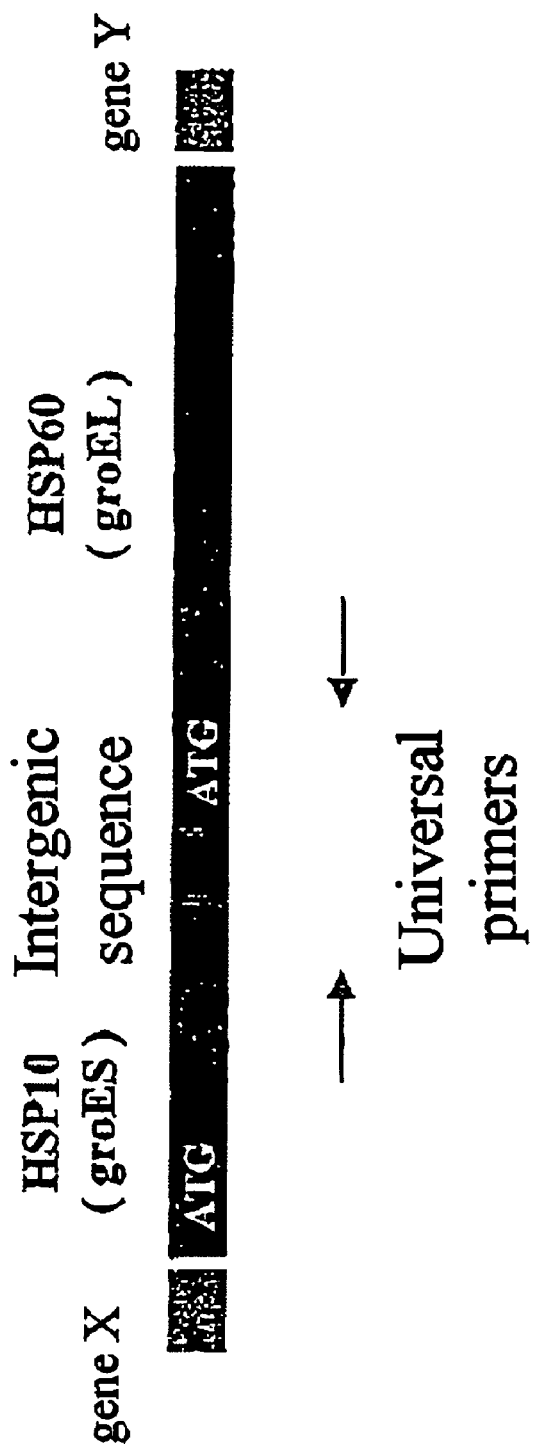
FIG. 2: Diagram of the groESL operon of *E. coli*. The universal primers are used to amplify the intergenic sequence.
Figure 3:
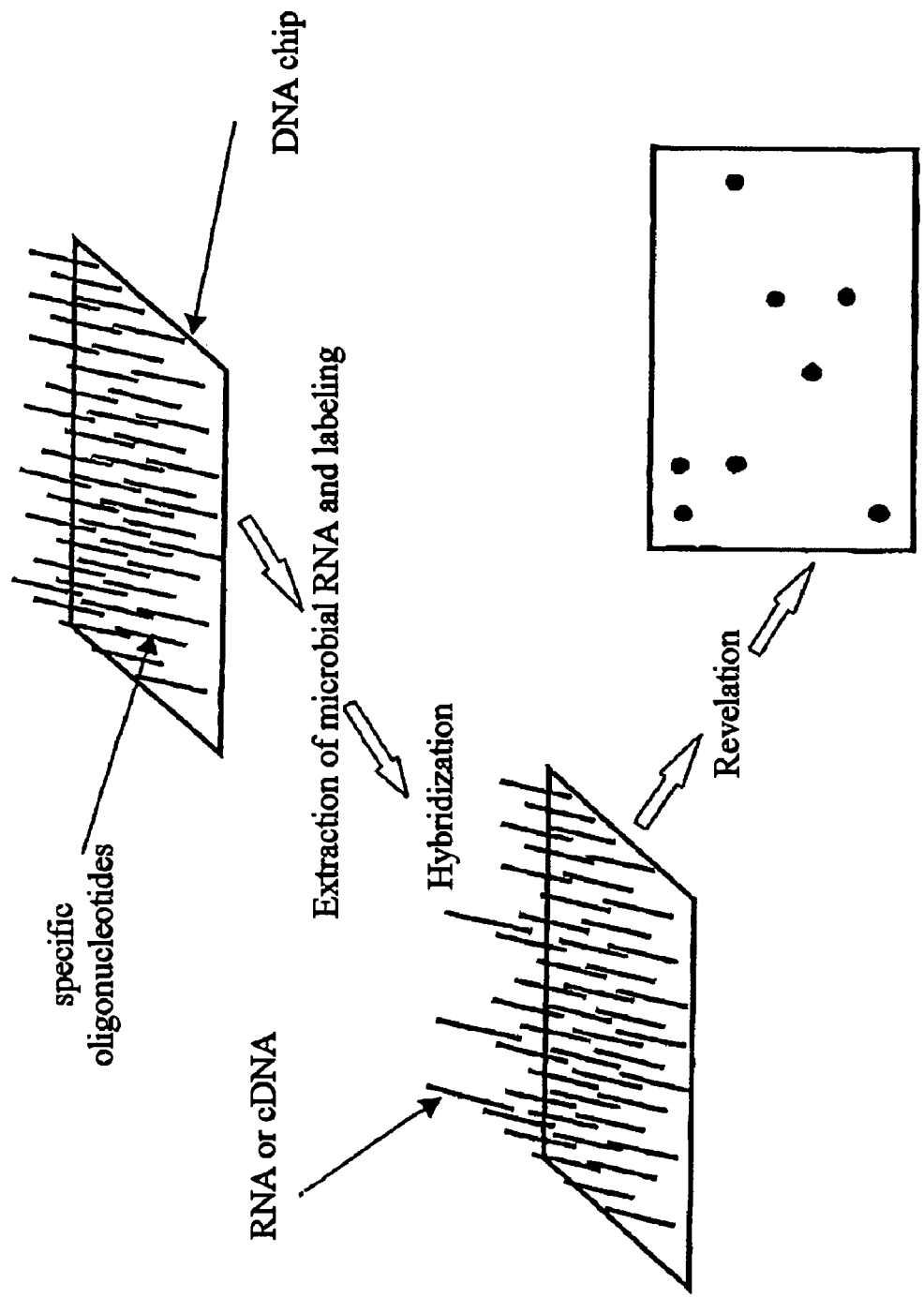
FIG. 3: Principle of a DNA chip. Specific sequences are attached to a solid support. The possible hybridization of the complementary sequences makes it possible to determine their presence in a sample.

In order to have a broad and representative sample of human colonic flora, it is necessary to isolate new bacterial strains, also called nonculturable (and therefore unknown) strains, which constitute a high percentage of the bacteria of the human colonic flora.

In order to perform these isolations, a large quantity of human stools is collected and sterilized by means of gamma-type radiation or by heat, for the purpose of sealing therein samples of these same human stools and of culturing them aerobically and anaerobically, in liquid and solid media.

Depending on the culture conditions used, it is thus possible to isolate new genera, species or strains of colonic bacteria or other eukaryotic microorganisms.

Example 2

Characterization of the Sequences of the Isolated Strains (rpoB)

This involves carrying out the molecular characterization of sequences, ideally of mRNA to perform a quantification, and if not of genomic DNA, of the isolates of bacterial or eukaryotic microorganisms.

The sequences corresponding to portions of the bacterial rpoBC operon are studied. The genes of this operon are in fact relatively homologous between genera.

A computer analysis (sequence alignment) thus makes it possible to define degenerate primers for amplifying the region which is heterologous between species and which corresponds to the transcribed intergenic region.

Thus, the primers SEQ ID NO: 1 and SEQ ID NO: 31, and also the other primers, were defined after alignment of the sequences corresponding to more than 50 species of living organisms (prokaryots and eukaryots, not shown) using the redundancy of the genetic code. The sequences SEQ ID NO: 53 and SEQ ID NO: 54 are in particular preferred.

The regions amplified by PCR or RT-PCR with the abovementioned primers can obviously be cloned into various vectors, in order to be used to refine the analysis (in particular in order to sequence them).

Example 3

Characterization of the Sequences of the Isolated Strains (GroESL)

The sequences corresponding to portions of the bicistronic bacterial GroESL operon are studied. The genes of this operon are in fact relatively homologous between genera.

Computer analysis (sequence alignment) thus makes it possible to define degenerate primers for amplifying the region which is heterologous between species and which corresponds to the transcribed intergenic region.

Thus, the primers SEQ ID NO: 34 and SEQ ID NO: 35 were defined after alignment of the sequences corresponding to more than 100 species of living organisms (prokaryots and eukaryots, not shown).

The sequences SEQ ID NO: 36 to SEQ ID NO: 52, and in particular SEQ ID NO: 139, correspond to complementary sequences which can be used to amplify microorganisms of diverse genera and/or families.

As regards the primers SEQ ID NO: 32 and SEQ ID NO: 33, they were defined based on the conserved sequences of the GroES and GroEL genes of E. coli, using the degenerative genetic code.

Example 4

Amplification Reactions (GroESL)

The PCR reactions are carried out according to the following protocol:

2 ml of culture broth shaken at 37° C. for 18 h are concentrated by centrifugation and resuspension of the bacterial pellet in 30 µl of distilled water, and then a ⅒ dilution of this concentrate, treated at 100° C. for 10 minutes, is used as a matrix for the PCR reactions. The reaction conditions are 94° C./5 min, then 25 cycles of (94° C./30 sec, 60° C./45 sec, 72° C./30 sec), followed by an elongation step at 72° C. for 7 min.

Analysis of the amplificates makes it possible to show that it is possible to amplify, using the primers SEQ ID NO: 32 and SEQ ID NO: 33, the intergenic region of various enterobacteria, such as *Escherichia coli, Enterobacter clocae, Morganella morganii, Serratia licquefasciens, Proteus mirabilis, Serratia marcescens, Klebsiella pneumoniae, Citrobacter freundii* or *Klebsiella oxytoca*. The amplified region varies in length, according to the species, from 400 to 500 base pairs (bp). Use of the pair SEQ ID NO: 34 and SEQ ID NO: 36 gives amplificates of between 550 and 650 bp in length.

Use of the pairs: (SEQ ID NO: 34, SEQ ID NO: 35 or SEQ ID NO: 39)/(a sequence chosen from the sequences SEQ ID NO: 36 to SEQ ID NO: 38 or SEQ ID NO: 40 to SEQ ID NO: 52, or SEQ ID NO: 139) makes it possible to amplify sequences specific to certain families and species, and to identify the organisms of these families or species.

For the amplification reactions, use is preferably made of a primer marked "A" with a primer marked "B".

The regions amplified by PCR or RT-PCR with the abovementioned primers can obviously be cloned into various vectors, in order to be used to refine the analysis (in particular in order to sequence them).

PCR Protocol

In order to show that using the intergenic region of the two operons of interest as a nucleic acid probe can make it possible to discriminate several bacterial species, said IGR for each target was amplified by direct PCR on bacterial suspensions. For the amplification reactions, use is preferably made of a primer marked "A" with a primer marked "B".

2 ml of culture broth shaken at 37° C. for 18 h are concentrated by centrifugation and resuspension of the bacterial pellet in 30 µl of distilled water, and then a ⅒ dilution of this concentrate, treated at 100° C. for 10 minutes, is used as a matrix for the PCR reactions.

groESL Operon:

The PCR reactions for this target are carried out at a Tm ranging between 59° C. and 60° C. The reaction conditions are 94° C./5 min, then 25 cycles of (94° C./30 sec, 60° C./45 sec, 72° C./30 sec), followed by an elongation step at 72° C. for 7 min. The amplified intergenic regions are then observed by agarose gel electrophoresis using a 1 Kb+ladder (Gibco BRL).

Analysis of the amplificates makes it possible to show that it is possible to amplify, using the primers SEQ ID NO: 32 and SEQ ID NO: 33, the intergenic region of various Enterobacteria, such as *Escherichia coli, Enterobacter clocae, Morganella morganii, Serratia licquefasciens, Proteus mirabilis, Serratia marcescens, Klebsiella pneumoniae, Citrobacter freundii* or *Klebsiella oxytoca*. The amplified region varies in length, according to species, from 400 to 500 base pairs (bp). Use of the pair SEQ ID NO: 34 and SEQ ID NO: 36 gives amplificates of between 550 and 650 bp in length.

rpoB/C Operon:

The PCR reactions for this target are carried out at a Tm ranging between 63° C. and 64° C. The reaction conditions are 94° C./4 min, then 30 cycles of (94° C./30 sec, 64° C./30 sec, 72° C./3 min), followed by an elongation step at 72° C. for 12 min. The amplified intergenic regions are then observed by agarose gel electrophoresis using a molecular weight marker III DNA ladder (ref: NO: 528552; Boehringer Mannheim).

Analysis of the amplificates makes it possible to show that it is possible to amplify, using the pair of primers SEQ ID NO: 53 and SEQ ID NO: 54, the intergenic region of the various bacteria, such as *Escherichia coli, Clostridium leptum, Klebsellia oxytoca, Lactococcus lactis, Citrobacter freundii, Serratia marcescens, Proteus mirabilis, Serratia liquefaciens, Morganella morganii, Enterobacter cloacae* or *Ruminococcus hydrogenotrophicus*.

DNA fragments corresponding to the intergenic regions of the rpoB/C operon in various species were reamplified and analyzed using bands extracted from an agarose gel preparation. These fragments were prepurified with a Qiagen extraction kit.

The regions amplified by PCR or RT-PCR with the abovementioned primers can obviously be cloned into various vectors, in order to be used to refine the analysis (in particular in order to sequence them).

Hybridization Protocol

With a view to testing the specificity of the PCR products, for the species selected for our study, deposits of these DNAs were made on a nylon membrane according to a sodium hydroxide (NaOH) fixation protocol. The DNA concentrations for these deposits are given on the corresponding figures. These membranes were hybridized according to the protocol of the PCR DIG Probe Synthesis Kit (Roche) Cat. NO: 1636090. The concentration of the probe used, synthesized according to the same protocol, is also indicated on the figures, as is the temperature of hybridization carried out overnight (18 h). The temperature of pre-hybridization is 65° C. for each experiment, and it lasts 45 min.

Detection of this type of hybridization with this type of labeling (DIG) is termed colorimetric ("cold" labeling different from radioactive labeling).

Figure 4:
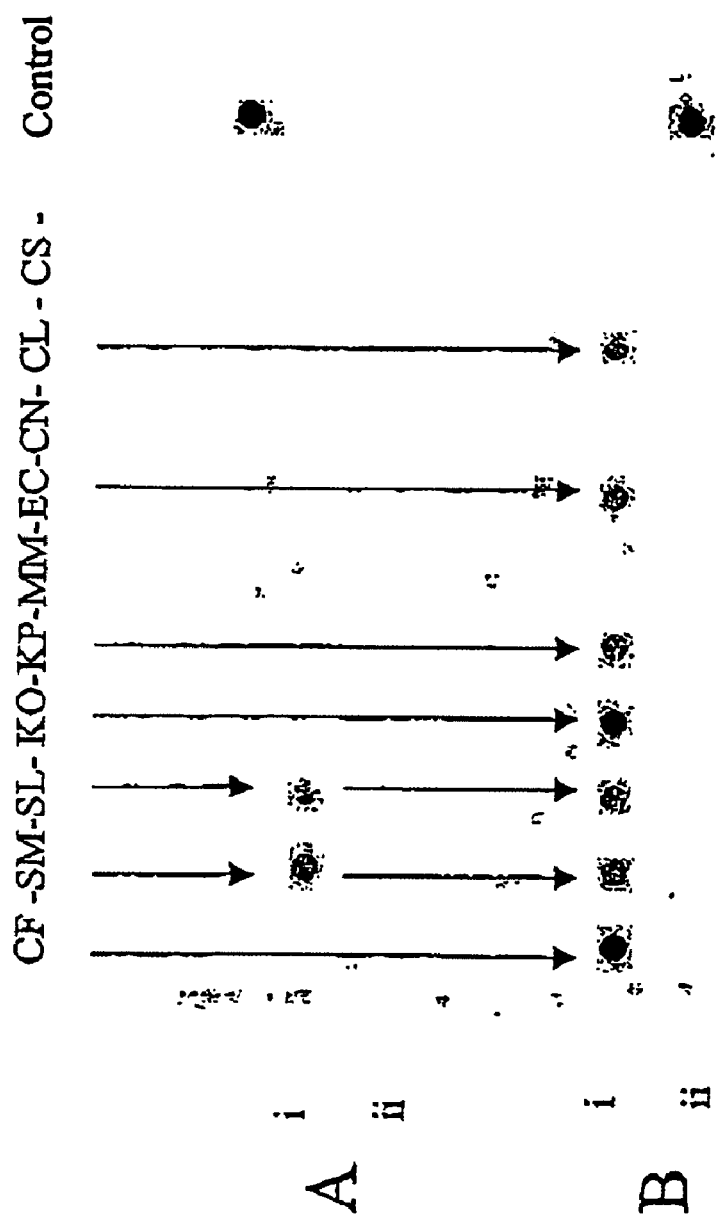
FIG. 4: Hybridization of deposits of 10 ng of DNA amplified by PCR with rpoBC primers (i) and of genomic DNA (ii), with a Serratia marcescens probe (~0.25 ng/ml) (A) or a Klebsiella oxytoca probe (~1 ng/ml) (B) for 18 hours at 60° C. and revelation for 30 minutes at 37° C. It is possible to observe cross hybridization of CF, SM, SL, EC and KP with the KO-DIG probe (~1 ng/ml) and of SL with the SM-DIG probe (~0.25 ng/ml).
Figure 5:
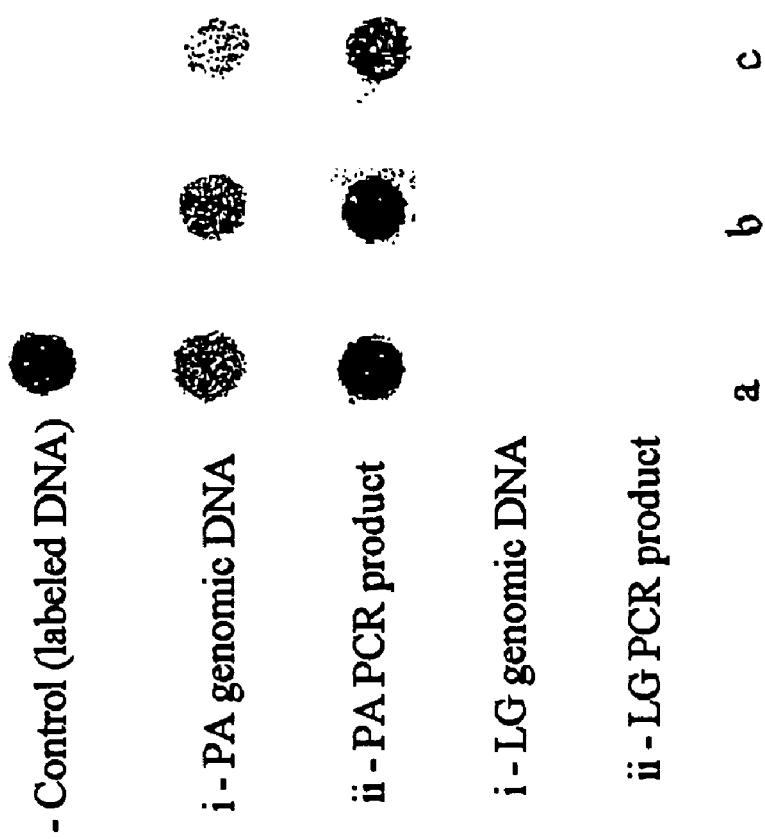
FIG. 5: Hybridization of deposits i (genomic DNA, a: 10 to 20 µg, b: 5 to 10 µg, c: 0.5 to 1 µg, d: 50 to 100 ng, e: 5 to 10 ng, f: 0.5 to 1 ng) and ii (DNA amplified by PCR with GroESL primers. a: 50 to 100 ng, b: 5 to 10 ng, c: 0.5 to 1 ng, d: 50 to 100 pg, e: 5 to 10 pg, f: 0.5 to 1 pg) with a PA-DIG probe (~10 ng/ml) for 18 hours at 42° C. and revelation for 30 min at 37° C.
Figure 6:
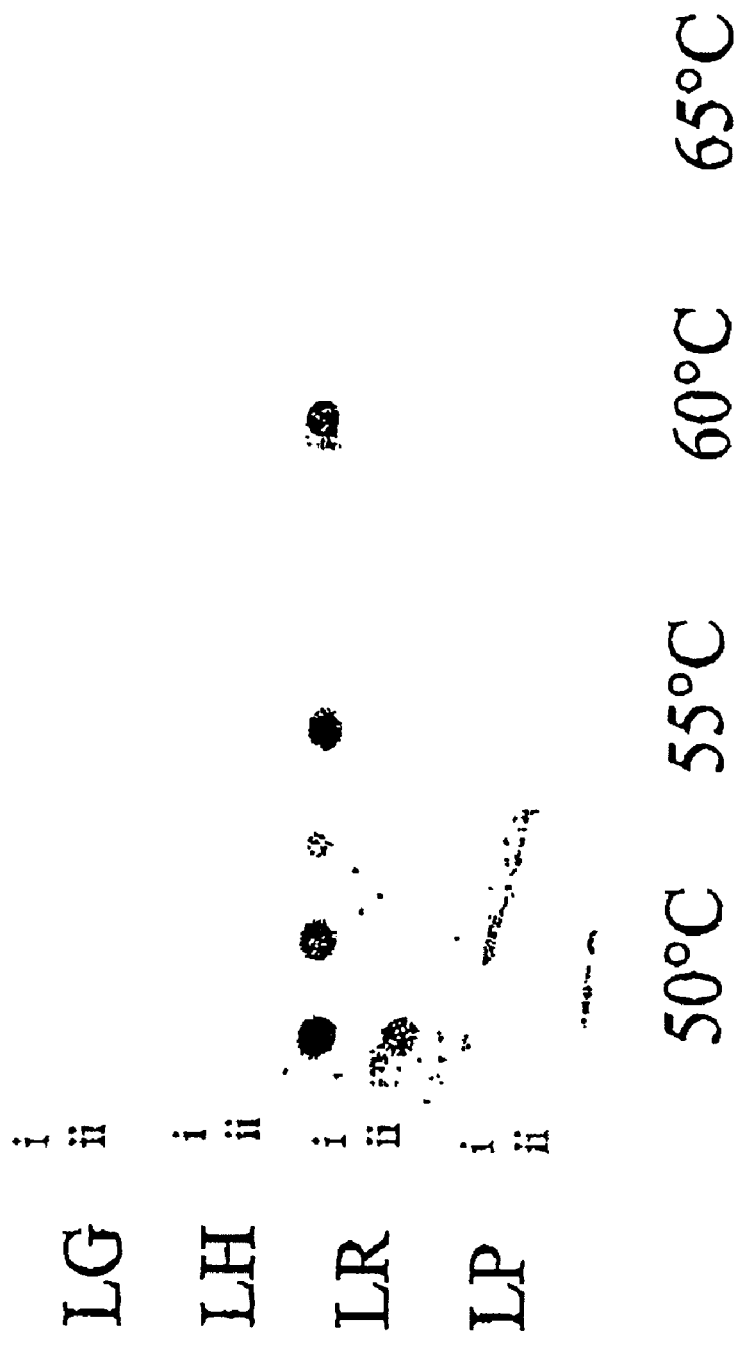
FIG. 6: Hybridization of deposits i (DNA amplified by PCR with rpoBC primers: 10 ng/1 ng/100 pg) and ii (genome DNA: 1 µg/100 ng/10 ng) with an LR-DIG probe (~1 ng/ml) for 18 hours at 50, 55, 60 and 65° C. and revelation for 30 min at 37° C.

FIGS. 4 to 6 show a specificity detection as a function of the organisms, although some crosshybridization reactions may exist. These reactions may be reduced by choosing probes which are shorter and located among the hypervariable intergenic sequences, as defined by SEQ ID NO: 63 to SEQ ID NO: 138 (rpoN) or SEQ ID NO: 40 to SEQ ID NO: 189 (GroESL).

Thus, a DNA chip with various probes located in the intergenic region will make it possible to recognize without hesitation the presence or absence of a microorganism, even when there is crosshybridization. Specifically, the presence of a microorganism will be deduced from the hybridization for each of the probes.

It may therefore be advantageous to define DNA chips having specific probes corresponding to the intergenic region of each microorganism, but also to include several different probes for each microorganism.

REFERENCES

{1}—Welling, et al., *Applied Environmental Microbiology*, 64:3336-45, 1998: Variations of bacterial populations in human feces measured by fluorescent in situ hybridization with group-specific 16S rRNA-targeted oligonucleotide probes.

{2}—Greisen, et al., Journal of Clinical Microbiology, 32:335-351, 1994: Staphylococcal identification using PCR amplification of 16S rDNA genes.

{3}—Jensen, et al., Applied Environmental Microbiology, 59:945-952, 1994: Staphylococcal identification using PCR amplification of spacer regions between 16S and 23S genetic loci.

{4}—Plikaytis, et al., above; Telenti, et al., above: PCR strategies for Mycobacterial speciation requiring the detection of restriction site polymorphisms (RFLP) within amplified products.

{5}—Zoetendal, Akkermans and De Vos, *Applied Environmental Microbiology*, 64:3854-9 (1998): Temperature gradient gel electrophoresis analysis of 16S rRNA from human fecal samples reveals stable and host-specific communities of active bacteria.

{6}—Vaitilinggom, Gendre and Brignon, *Applied Environmental Microbiology* 64:1157-60, 1998: Direct detection of viable bacteria, molds, and yeast by reverse transcriptase PCR in contaminated milk samples after heat treatment.

{7}—Gendre and Brignon, Compagnie Gervais Danone, patent # PCT/FR97/01918 WO 98/18958 (1998): Method for detecting live microbiological contaminants in a food product sample.

{8}—Doré, et al., *Applied Environmental Microbiology*, 65:4799-807, 1999: Direct analysis of genes encoding 16S RNA from complex communities reveals many novel molecular species within human gut.

{9}—Goh, Chow and Hemmingsen, U.S. Pat. Nos. 5,708, 160 (1998) & 5,989,821 (1999).

{10}—Emelyanov and Sinitsyn, *Russian Journal of Genetics*, 35:618-627, 1999: A GroE-based phylogenetic analysis shows a very close evolutionary relationship between mitochondria and rickettsia.

The invention claimed is:

1. A method for detecting microorganisms of a bacterial flora which have an rpoBC operon in common, wherein the rpoBC operon comprises a noncoding intergenic region, the method comprising:
   a) preparing genomic DNA or mRNAs of said flora,
   b) amplifying at least 20 or more nucleotides of a noncoding intergenic region between two genes,
      wherein the two genes are an rpoB gene and an rpoC gene,
      wherein the region is located in the rpoBC operon, and
   c) identifying the various intergenic regions amplified in order to determine the microorganisms of said flora which have at least one rpoBC operon in common.

2. The method as claimed in claim 1, wherein the identification of the amplified regions is carried out utilizing sequences complementary to the sequences of said noncoding intergenic region between the rpoB and rpoC genes from the microorganisms of said flora.

3. The method as claimed in claim 1, wherein said noncoding intergenic region between the rpoB and rpoC genes is amplified utilizing primers located in coding sequences of the rpoB and rpoC genes.

4. The method as claimed in claim 3, wherein said primers are SEQ ID NO: 53 and SEQ ID NO: 54.

5. The method as claimed in claim 4, wherein said microorganisms which have an rpoBC operon in common belong to *Escherichia coli, Clostridium leptum, Kiebsellia oxytoca, Lactococcus lactis, Citrobacter freundii, Serratia marcescens, Proteus mirabilis, Serratia liquefaciens, Morganella morganii, Euterobacter cloachae* or *Ruminococcus hydrogenotrophicus* species.

* * * * *